(12) United States Patent
Escriou et al.

(10) Patent No.: US 6,723,559 B2
(45) Date of Patent: Apr. 20, 2004

(54) RECOMBINANT SEGMENTED NEGATIVE STRAND VIRUS CONTAINING BICISTRONIC VRNA SEGMENT WITH A DUPLICATION OF ITS 3' NONCODING FLANKING SEQUENCE, AND VACCINES AND THERAPEUTIC COMPOSITIONS CONTAINING THE SAME

(75) Inventors: Nicolas Robert Xavier Escriou, Paris (FR); Sylvie Van Der Werf, Gif sur Yvette (FR); Alexandre Vieira-Machado, Paris (FR); Nadia Naffakh, Malakoff (FR)

(73) Assignee: Institute Pasteur, Paris (FR)

( * ) Notice: Subject to any disclaimer, the term of this patent is extended or adjusted under 35 U.S.C. 154(b) by 0 days.

(21) Appl. No.: 10/123,170

(22) Filed: Apr. 17, 2002

(65) Prior Publication Data

US 2003/0008277 A1 Jan. 9, 2003

Related U.S. Application Data

(60) Provisional application No. 60/283,957, filed on Apr. 17, 2001.

(51) Int. Cl.[7] .......................... C12N 15/74; C12N 5/00; C12Q 1/70; C12P 21/04; C07H 21/04

(52) U.S. Cl. .......................... 435/320.1; 435/5; 435/6; 435/69.7; 435/325; 536/23.1; 536/23.72

(58) Field of Search ............... 435/5, 6, 69.7, 435/325, 320.1; 536/23.1, 23.72

(56) References Cited

U.S. PATENT DOCUMENTS 5,578,473 A 11/1996 Palese et al.
5,854,037 A 12/1998 Pales et al.

OTHER PUBLICATIONS

Stephan Pleschka et al., "A Plasmid–Based Reverse Genetics System for Influenza A Virus", Journal of Virology, Jun. 1996, p. 4188–4192.
Ramon Flick et al., "Transient Bicistronic vRNA Segments for Indirect Selection of Recombinant Influenza Viruses", Virology 262, pp. 93–103 (1999).

Primary Examiner—Hankyel T. Park
(74) Attorney, Agent, or Firm—Oblon, Spivak, McClelland, Maier & Neustadt, P.C.

(57) ABSTRACT

The present invention relates to recombinant negative strand RNA molecules which may be used to express heterologous proteins in animal cells and/or to construct recombinant viruses able to express heterologous proteins during their multiplication in host animal cells.

44 Claims, 11 Drawing Sheets

| | CAT Level |
|---|---|
| pPRNA35 | <0.1 |
| pPRNA35-CAT | 160 |
| pPRNA37 | <0.1 |
| pPRNA37-CAT | 1.4 |
| pPRNA38 | <0.1 |
| pPRNA38-CAT | 132 |

Expt 1:

WSN            vNA35        vNA35-CAT C1/3 vNA35-CAT C2/3  vNA35-VP0c C1  vNA35-VP0c C2

Expt 2:

| WSN | vNA35 | vNA35-CAT C1/3 |
|---|---|---|
| vNA38 | vNA38-CAT C1 | vNA38-CAT C2 |

|  | 8 h pi | 24 h pi |
|---|---|---|
| vNA35 #101 | 0 | 0 |
| vNA35-CAT C1/3 | 1.8 | 17 |
| vNA35-CAT C2/3 | 0.39 | 6.6 |
| vNA38 AC1/H | 0 | 0 |
| vNA38-CAT AC1/H | 430 | 5000 |
| NA38-CAT AC2/H | 390 | 5900 |

FIG. 9

| Construct | Transient expression at 48 hours (Plasmid transfecton) | Expression after infection with several independant viral clones (mean±SD) | |
|---|---|---|---|
| | | 24 h p.i. | a 48 h p.i. |
| NA38 | <0.1 ng/ml | <0.1 ng/ml | <0.1 ng/ml |
| NA38-S | 5,7 ng/ml | 5±2,8 ng/ml | 23±14 ng/ml |

FIG. 12

RECOMBINANT SEGMENTED NEGATIVE STRAND VIRUS CONTAINING BICISTRONIC VRNA SEGMENT WITH A DUPLICATION OF ITS 3' NONCODING FLANKING SEQUENCE, AND VACCINES AND THERAPEUTIC COMPOSITIONS CONTAINING THE SAME

CROSS-REFERENCE TO A RELATED APPLICATION

The present application claims priority to U.S. Provisional Application No. 60/283,957 filed Apr. 17, 2001.

BACKGROUND OF THE INVENTION

1. Field of the Invention

The present invention relates to recombinant negative strand RNA molecules which may be used to express heterologous proteins in animal cells and/or to construct recombinant viruses able to express heterologous proteins during their multiplication in host animal cells.

2. Discussion of the Background

Despite the segmented nature of the influenza virus genome, several approaches have already been described to achieve the construction of stable recombinant influenza viruses, able to express heterologous protein sequences of interest. These approaches have been made possible after the development of reverse genetics techniques for the influenza viruses.

Short foreign polypeptides can be expressed by inserting the foreign sequence into an essential viral gene (see, for example, Castrucci, M. R., S. Hou, P. C. Doherty, and Y. Kawaoka 1994. Protection against lethal lymphocytic choriomeningitis virus (LCMV) infection by immunization of mice with an influenza virus containing an LCMV epitope recognized by cytotoxic T lymphocytes *Journal of Virology.* 68:3486-90). This strategy is limited to the use of small size epitope inserts and the insertion of a foreign epitope into the sequence of a viral protein can modify the protein in a way which would prevent the generation of viable recombinant viruses Longer polypeptides can be expressed by the use of a fusion protein containing a protease sensitive peptide sequence between an essential viral gene product and a foreign polypeptide (Percy, N., W. S. Barclay, A. Garcia Sastre, and P. Palese 1994. Expression of a foreign protein by influenza A virus *Journal of Virology.* 68:4486-4492), but this approach results in the expression of altered viral and/or foreign proteins due to the presence of the specific protease signal in the cleaved protein products.

A foreign polypetide can also be expressed via the use of recombinant RNA segment which were made functionally dicistronic or tricistronic at the level of translation by the insertion of the IRES (Internal Ribosome Entry site) of the human BiP RNA (Garcia-Sastre, A., T. Muster, W. S. Barclay, N. Percy, and P. Palese 1994. Use of a mammalian internal ribosomal entry site element for expression of a foreign protein by a transfectant influenza virus *Journal of Virology.* 68:6254-6261). In this case, the bicistronic mRNA (which is transcribed during viral replication) permits internal initiation of translation of viral sequences (via internal binding of the ribosome to the IRES sequence) and allows for the expression of foreign protein coding sequences via cap-dependant initiation of translation. A potential drawback of this approach could rely in the fact that the synthesis of the NA gene, which is under the dependance of the IRES sequence is not regulated to the same level and/or at the same time point as it is in the wild type virus ; this could modify the phenotypic characteristics of the virus as it has been shown, for example, that the amount of NA incorporated in the influenza virions affects the infectivity of the viral particles.

Garcia-Sastre et al. (Garcia-Sastre, A., N. Percy, W. Barclay, and P. Palese 1994. Introduction of foreign sequences into the genome of influenza A virus *Developments in Biological Standardization.* 82:237-246) reported the design of a similar dicistronic RNA molecule in which the corresponding mRNA contains the viral sequence in a proximal position which allows translation from the regular terminal open reading frame, while the translation of the foreign sequence would be initiated from an internal site. In this publication, the IRES of the EMCV virus was used but turned out to be non functional in influenza virus infected cells, since no expression of the foreign sequence could be detected. What is noticeable here is the presence of a duplication of the 39 last nucleotides of NA ORF, which extended the 5' terminus of the recombinant vRNA molecule from the 28 nt of the 5' non coding region itself to the 67 first nucleotides of the 5' terminus of the original NA segment of virus WSN. Nevertheless, this duplication seemed to arise from a facility in the genetic construction of the RNA molecule, since any data neither demonstrates nor shows the role of these additional 39 nt at the 5' end of the recombinant NA segment encoded by the pT3NA/EMC and pT3NA/EMC-NS 1 plasmids.

More recently, Flick and Hobom (Flick, R., and G. Hobom 1999. Transient bicistronic vRNA segments for indirect selection of recombinant influenza viruses *Virology.* 262:93-10) introduced another principle of constructing dicistronic vRNA molecules for the transient expression of foreign sequences and/or selection genes. They showed that a recombinant vRNA-like molecule can be made dicistronic by the duplication of its 3'-non coding flanking sequence : in this case, the recombinant RNA molecule is functionally bicistronic for its replication and transcription, in the sense that it can be transcribed and replicated in (a) a genomic mode after interaction of the single 5' non coding sequence with the external 3' non coding sequence and in (b) a subgenomic mode after interaction of the 5' non coding sequence with the internal 3' non coding sequence. Two types of mRNA molecules are produced, genomic mRNA allows translation of the first cistron, whereas the shorter subgenomic mRNA drives the translation of the second cistron. They showed that the recombinant dicistronic RNA molecules can be propagated as an additional ninth segment during a few rounds of viral multiplication, but that next, the distal segment is spontaneously lost through vRNA-internal initiation events, giving rise to a monocistronic ninth segment. Moreover, it can be anticipated that this resulting virus will be unstable since additional, independant vRNA segments coding for foreign genes are lost during virus growth in the absence of continuing selective pressure as it has been reported by others and the authors themselves in another publication (Neumann, G., and G. Hobom 1995. Mutational analysis of influenza virus promoter elements in vivo *Journal of General Virology.* 76:1709-17).

Based on the disadvantages of the prior studies, the present inventors sought to design dicistronic influenza genomic segments, in which the first cistron would drive the translation of an essential viral gene and the second cistron would permit the translation of foreign sequences. In completing the invention the present inventors demonstrate that such dicistronic viral segment permitted the rescue of stable recombinant influenza viruses, able to express foreign sequences of interest. The inventors further demonstrate that such recombinant influenza viruses may be used to express heterologous proteins in an animal host. In particular, when inoculated in an animal recipient, these recombinant viruses are able to induce an immune response against the encoded foreign protein. It should be underlined that Flick and Hobom neither reported nor suggested the construction of such dicistronic genomic segments or related recombinant viruses.

The present inventors, for the first time, demonstrate the effectiveness of using recombinant RNA molecules, which were made functionally dicistronic or multicistronic at the level of RNA replication and transcription.

SUMMARY OF THE INVENTION

Objects of the Present Invention are as Follows:

A recombinant RNA molecule comprising, from the 3' end towards the 5' end:
a) At least two units, each of them composed of a wild-type truncated or mutated 3'-non coding flanking sequence of a genomic RNA segment of a segmented negative strand RNA virus, optionay a given spacer sequence of a size chosen from 0 nucleotide to 500 nucleotides, the reverse complement of an mRNA coding sequence or of a fragment of an mRNA coding sequence linked in frame to an initiating AUG and termination codon, a second spacer sequence of a size choosen from 0 nucleotide to 500 nucleotides.
b) A wild-type, truncated or mutated 5'-non coding flanking sequence of a genomic RNA segment of a segmented negative strand RNA virus A recombinant RNA molecule as described above, wherein the spacer sequence of step A) has preferably a size choosen from 15 to 150 nucleotides.

The recombinant RNA molecule as described above, wherein the first unit, located at the 3' extremity of the RNA molecule, comprises the reverse complement of the coding sequence selected from the group consisting of a nonmutated viral protein, mutated viral protein, a truncated viral protein, and a chimeric viral protein.

A recombinant virus comprising a segmented negative strand virus, in which at least one genomic segment has been substituted with the recombinant RNA molecule as described above.

The recombinant virus as described above, wherein the first unit, located at the 3' extremity of the recombinant RNA segment contains the reverse complement of the coding sequence for the viral protein which was encoded by the substituted segment.

The recombinant virus as described above, wherein the virus is a virus choosen among the Orthomyxoviridae, Bunyaviridae or Arenaviridae families.

The recombinant virus as described above, wherein the virus is an influenza virus.

The recombinant virus as described above, in which the substituted genomic segment contains only two units and the second unit comprises the reverse complement of an mRNA coding sequence for an heterologous protein of interest.

The recombinant virus as described above, in which the substituted genomic RNA segment of a segmented negative strand virus is the neuraminidase (NA) segment (segment 6) of influenza virus.

The recombinant virus as described above, in which the 5'-non coding flanking sequences of the recombinant RNA segment are replaced by a longer polynucleotide RNA fragment from the 5' end of an influenza genomic RNA segment A purified polynucleotide comprising:
a) a wild-type, truncated or mutated 3' noncoding flanking viral sequence of a genomic RNA segment of a segmented negative strand RNA virus associated upstream with the reverse complement of a viral Open Reading Frame of a segmented negative strand RNA virus,
b) at least one sequence constitued by a wildtype, truncated or mutated 3' noncoding flanking sequence of a genomic RNA segment of a segmented negative strand RNA virus associated upstream with a reverse complement Open Reading Frame with a heterologous Open Reading Frame or a polynucleotide of interest, and
c) a wild-type, truncated or mutated 5' non coding viral sequence.

A purified polynucleotide as described above comprising:
a) a wild-type, truncated or mutated 3' noncoding flanking viral sequence of a genomic RNA segment of a segmented negative strand RNA virus associated upstream with the reverse complement of a viral Open Reading Frame of a segmented negative strand RNA virus,
b) at least one sequence constituted by a duplication of the same 3' noncoding flanking sequence associated upstream with the reverse complement of a heterologous gene or a polynucleotide of interest,
c) a wild-type, truncated or mutated 5' noncoding sequence of the same origin as the 3' noncoding sequence above.

A recombinant segmented negative strand RNA virus comprising a purified polynucleotide as described above, wherein said purified polynucleotide comprises at least one or more duplication of its 3 ' noncoding flanking sequence with upstream one or more heterologous genes of interest in at least one of its genome segments.

A recombinant segmented negative strand RNA virus comprising a purified polynucleotide as described above which comprises a spacer located upstream the heterologous gene of interest and downstream the 5' noncoding flanking sequence, wherein said spacer corresponds to at least one or more nucleotide of the genomic RNA segment of a segmented negative strand RNA virus up to the entire sequence, said sequence has been made non coding by the disruption of its Open Reading Frame.

A recombinant virus as described above wherein the virus is an Influenza virus.

A recombinant segmented negative strand virus comprising a purified polynucleotide as described above, wherein viral Open Reading Frame is encoding for the neuraminidase (NA).

A recombinant segmented negative strand virus comprising a purified polynucleotide as described above, wherein the spacer located upstream the heterologous gene of interest and dowstream the 5' noncoding flanking sequence correspond to at least the reverse complement of the 39 last nucleotides of a coding sequence plus termination codon of a segmented negative strand RNA virus.

A recombinant segmented negative strand virus comprising a purified polynucleotide as described above, wherein the spacer located upstream the heterologous gene of interest and downstream the 5' noncoding flanking sequence correspond to the reverse complement of the 39 last nucleotides plus termination codon of the neuraminidase gene of said virus.

A purified polypeptide encoded by a polynucleotide as described above and contained in a recombinant virus according to any one of 4 to 10, wherein said polypeptide has the biological characteristic to induce and/or modulate and/or increase the immune response in a host against viral bacterial, fungal or tumoral diseases.

A viral vector useful for delivering an adjuvant of immunity constitued by a recombinant virus as described above.

A viral vector useful for delivering of a biologically active protein of interest comprising the a recombinant virus as described above.

A composition comprising a recombinant virus as described above.

A vaccine composition comprising a recombinant virus as described above.

A method for the induction in the mucosal tissues of a protective response against an infectious agent or a tumoral disease comprising the delivery of a composition as described above.

A method for the induction of a protective response as described above, wherein the mucosal tissue is choosen among the nasal and/or the pulmonary tissues.

A method for producing a recombinant virus, comprising culturing an eucaryotic cell transfected with a vector as described above said cells being infected with a parental strain of a segmented negative strand RNA virus, and recovering the recombinant virus from the resulting culture.

A method as described above, wherein the recombinant virus is a recombinant influenza virus.

A therapeutic composition comprising a recombinant virus as described above.

A kit comprising a composition as described above.

A recombinant virus vNA38-CAT deposited at the C.N.C.M. on Apr. 12, 2001 under the accession number I-2657. A recombinant virus vNA38-S deposited at the CNCM on Apr. 15, 2002 under the accesion number I-2848.

A recombinant DNA molecule corresponding to the recombinant RNA molecule as described above after retrotranscription of said RNA.

A recombinant DNA molecule corresponding to the recombinant viral genome of the recombinant virus as described above after retrotranscription of said RNA.

A process for obtaining the expression in a human or animal host or in a culture of eukaryotic cells of a molecule of interest characterized by infecting said host or culture cells by a recombinant virus as described above.

A composition comprising the recombinant RNA molecule as described above and one or more pharmaceutically acceptable ingredients.

A composition comprising the recombinant segmented negative strand virus as described above and one or more pharmaceutically acceptable ingredients.

A composition comprising the purified polynucleotide as described above and one or more pharmaceutically acceptable ingredients.

A kit comprising the recombinant RNA molecule as described above and one or more reagents for assaying infectivity, immune response (CTL or antibody response), gene expression, or protein levels.

A kit comprising the recombinant segmented negative strand virus as described above and one or more reagents for assaying infectivity, immune response (CTL or antibody response), gene expression, or protein levels.

A kit comprising the purified polynucleotide as described above and one or more reagents for assaying infectivity, immune response (CTL or antibody response), gene expression, or protein levels.

Other objects of the present invention are vaccines comprising the recombinant RNA molecule, the recombinant segmented negative strand RNA virus and/or the purified polynucleotide admixed with one or more adjuvants.

Other objects of the present invention are methods of inducing a protective response against infectious agents or a tumoral disease comprising administering the recombinant RNA molecule, the recombinant segmented negative strand virus and/or the purified polynucleotide to a mucosal tissue. Preferably, the administering further comprises the administering of an adjuvant. In one embodiment of the invention, the a mucosal tissue is nasal mucosal tissue or pulmonary mucosal tissue.

Other objects of the present invention are compositions comprising the recombinant RNA molecules, the recombinant segmented negative strand viruses, and/or the purified polynucleotide and one or more pharmaceutically acceptable ingredients.

Other objects of the present invention are kits containing the recombinant RNA molecules and/or the recombinant segmented negative strand viruses and/or the purified polynucleotides and one or more reagents for assaying infectivity, immune response, gene expression or protein levels.

(a) shows CAT gene product expression by dicistronic NA35-CAT RNA molecule. Subconfluent monolayers of COS-1 cells ($3 \times 10^5$ cells in 35 mm dishes) were transfected by a mixture of plasmids pcDNA-NP, pcDNA-PA, pcDNA-PB1 and pcDNA-PB2 together with poll expression plasmid pPRNA35-CAT, pPRNA37-CAT or pPRNA38-CAT, as described in methods. At 48 hours post-transfection, cell extracts were prepared and assayed for CAT levels as described in methods. Levels are given in ng of CAT proteins for $10^6$ transfected cells.

(b) shows NA gene expression by dicistronic NA35-CAT RNA molecule. COS-1 cells grown in 35-mm dishes were transfected as described above. 48 hours post-transfection, cells were detached, labeled with the mouse monoclonal antibody 10C9, which is specific for the WSN-NA protein, and FITC-conjugated anti-mouse IgG antibodies and then analyzed for fluorescence intensity on a FACScalibur fluorocytometer, as described in methods.

(c) shows the presence of subgenomic vRNA like molecules in transfected cells. COS-1 cells grown in 35-mm dishes were transfected as described above. 48 hours post-transfection, total cellular RNA were prepared and analyzed by Northern Blot for the presence of genomic (G) and subgenomic (SG) vRNA with a positive sense riboprobe specific for CAT sequences, as described in methods. Position of molecular weight markers (kb) is indicated.

Figure 4:
Figure 4:
Figure 4:
Figure 4:
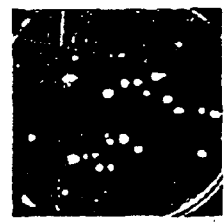
Figure 4:
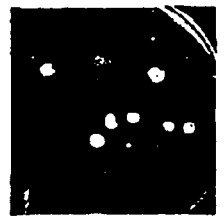
Figure 4:

FIG. 4: Rescue of infectious influenza viruses with dicistronic segment 6. Rescue of several dicistronic RNA molecules into stable and infectious influenza viruses was performed. The experiments depicted below show the plaque phenotype of the viruses when assayed on monolayers of MDCK cells. Independent viral clones were used; two independent experiments are reported.

Figure 5:
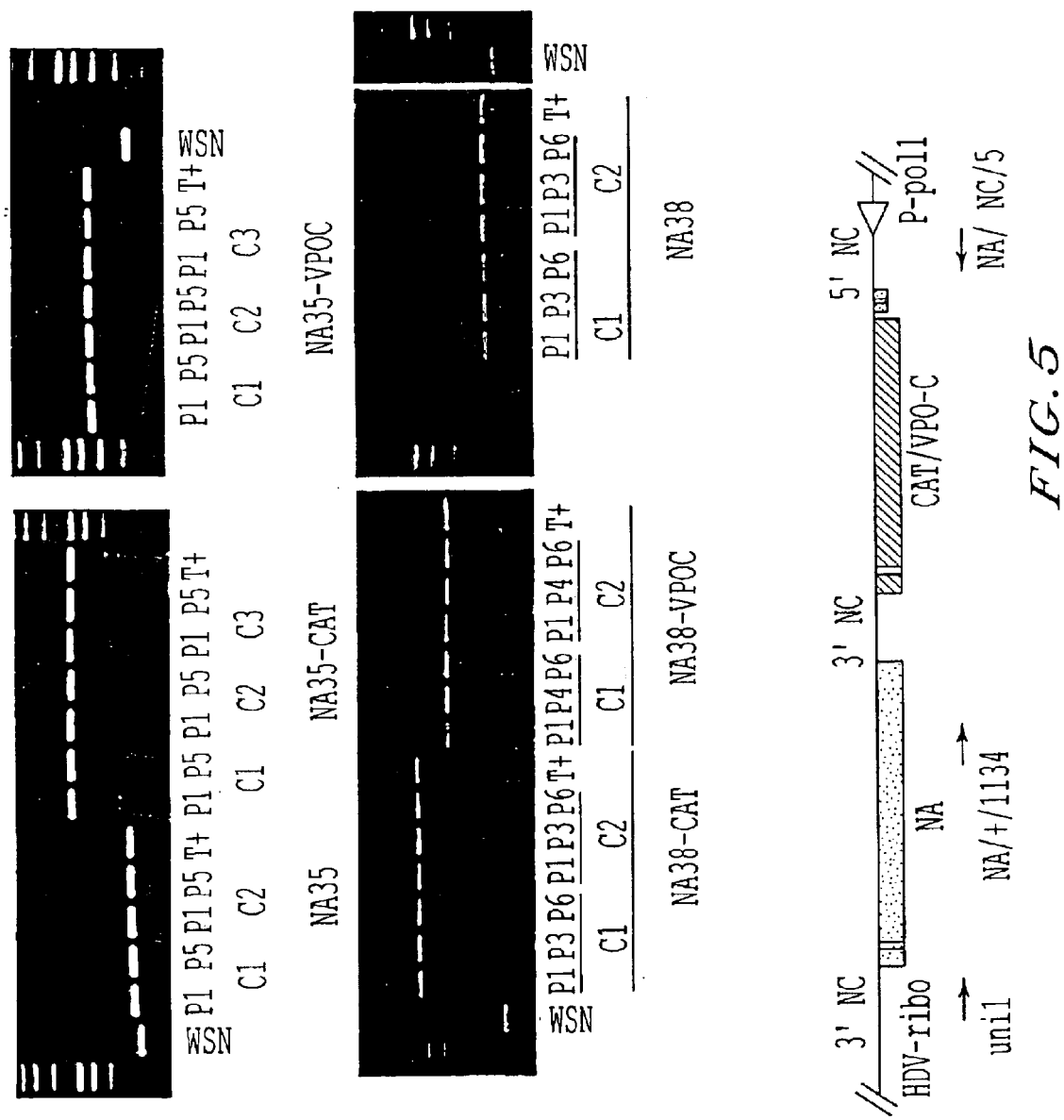

FIG. 5: Genetic Stability of the recombinant dicistronic viruses. vNA35 (2 clones), vNA35-CAT (3 clones) and vNA35-VPOc (3 clones) viruses vNA38 (2 clones) vNA38-vPoc (3 clones) were passaged 5 or 6 times on MDCK cells at an M.O.I. of 0.01. The RNA of the first, an intermediate and the last passages were prepared by TRIZOL™ extraction (Life Technologies). Next, their cDNAs were prepared by reverse transcription reaction, using the oligonucleotide uni-1 complementary to the last 12 bases of the 3' terminus of the WSN NA genomic segment. cDNAs were used as templates for a PCR reaction, using a pair of oligonucleotides, NA/+/1134 and NA/NC/5' , that allowed the amplification of the 3' vRNA internal promoter and the foreign sequence, as illustrated below. pPRNA (encoding the wt NA) and the plasmids used to generate the recombinant viruses were used as controls (T+).

Figures 6, 7:
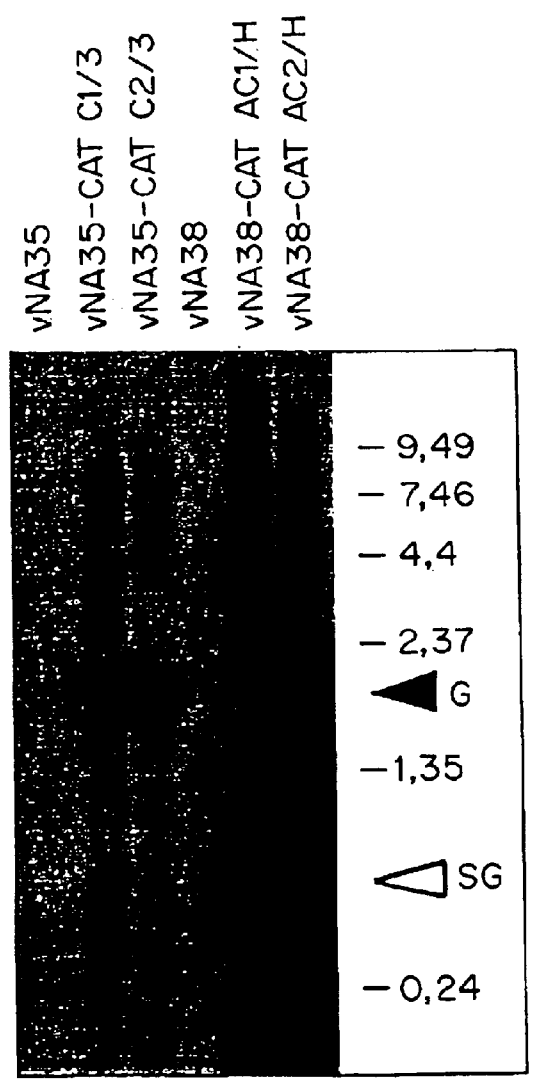

FIG. 6: Expression of the CAT gene product by the vNA35-CAT and vNA38-CAT viruses. Confluent monolayers of COS-1 cells were infected at an M.O.I of 2 with independant clones of the recombinant vNA35, vNA38, vNA35-CAT and vNA38-CAT influenza viruses at an M.O.I of 2. 8 and 24 hours after infection, cell extracts were prepared and assayed for CAT levels as described in methods. Levels are given in ng of CAT proteins per $10^6$ infected cells.

FIG. 7: Evidence for the presence of subgenomic vRNA like molecules in infected cells. COS-1 cells grown as a monolayer in 35-mm dishes were infected with either recombinant vNA35, vNA38, vNA35-CAT and vNA38-CAT viruses at an M.O.I of 2. 22 hours post-infection, total cellular RNA were prepared and analyzed by Northern Blot for the presence of genomic (G) and subgenomic (SG) vRNA with a positive sense riboprobe specific for CAT sequences, as described in methods. Position of molecular weight markers (kb) is indicated.

Figure 8A:
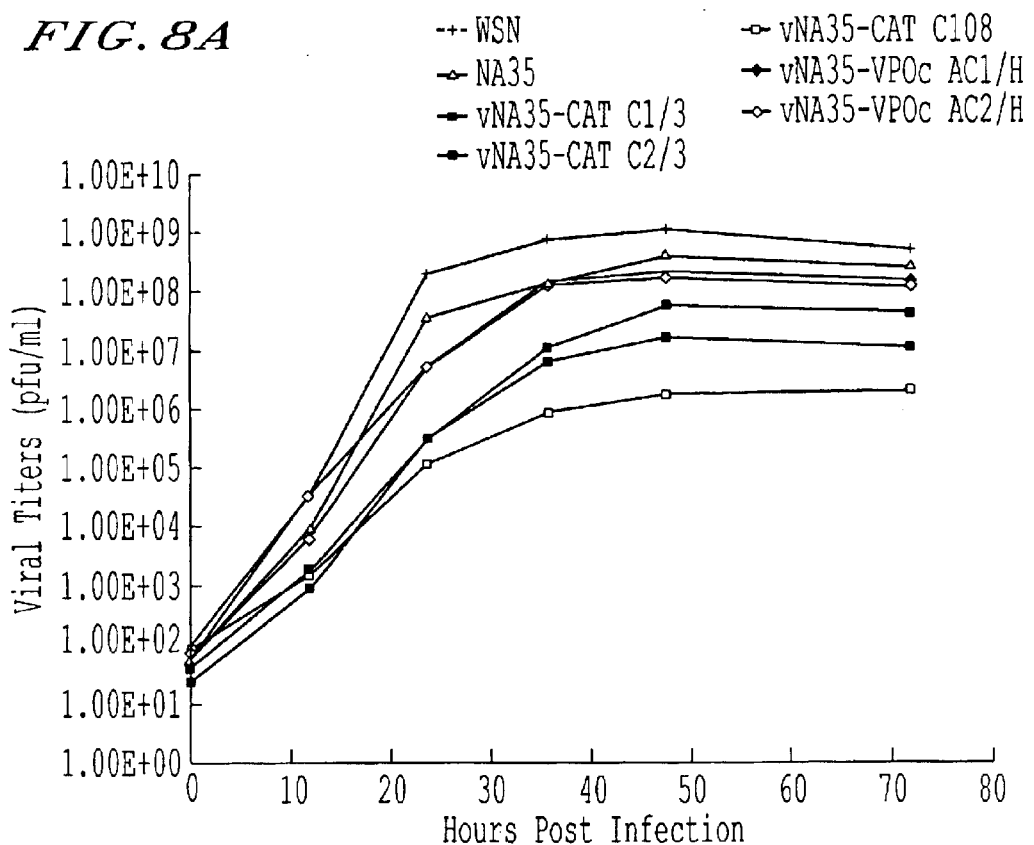
Figure 8B:
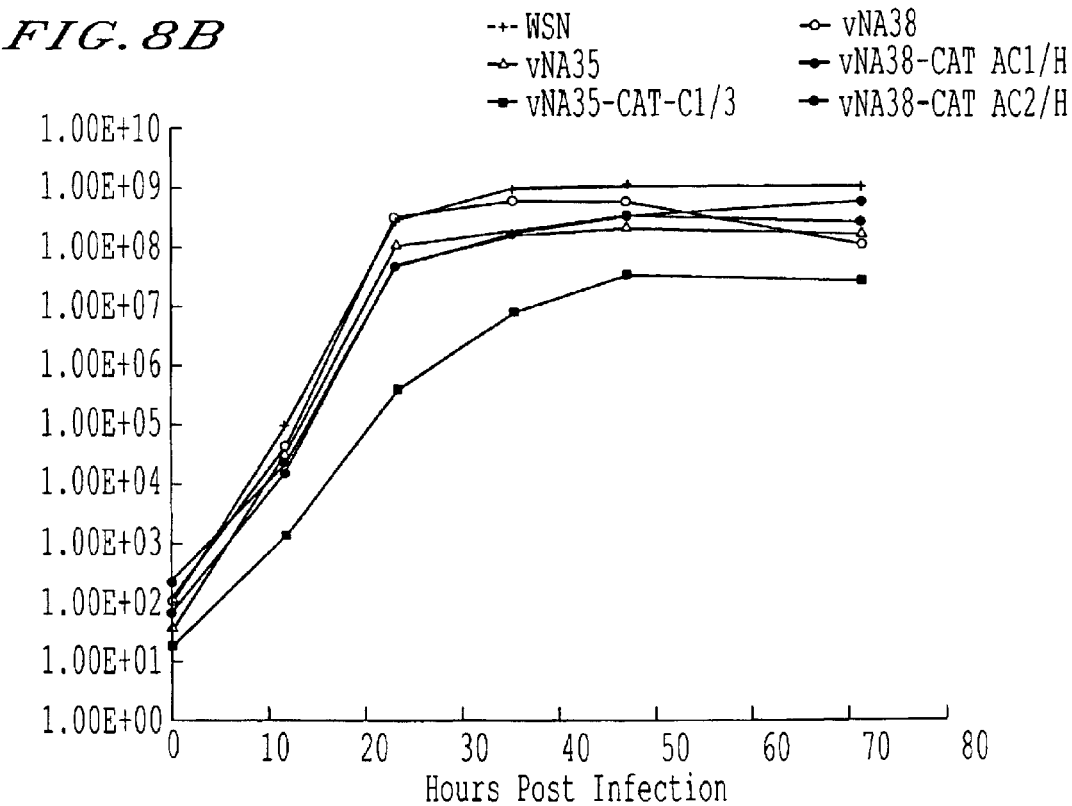

FIG. 8: Growth curves of the recombinant influenza viruses. Confluent monolayers of MDCK cells were infected with wild type WSN virus or independant clones of the indicated recombinant viruses at an MOI of 0.001. At the indicated time points, the supernatants were collected and titered for virus on MDCK cell monolayers, in a standard plaque assay (see methods).

Figure 9:
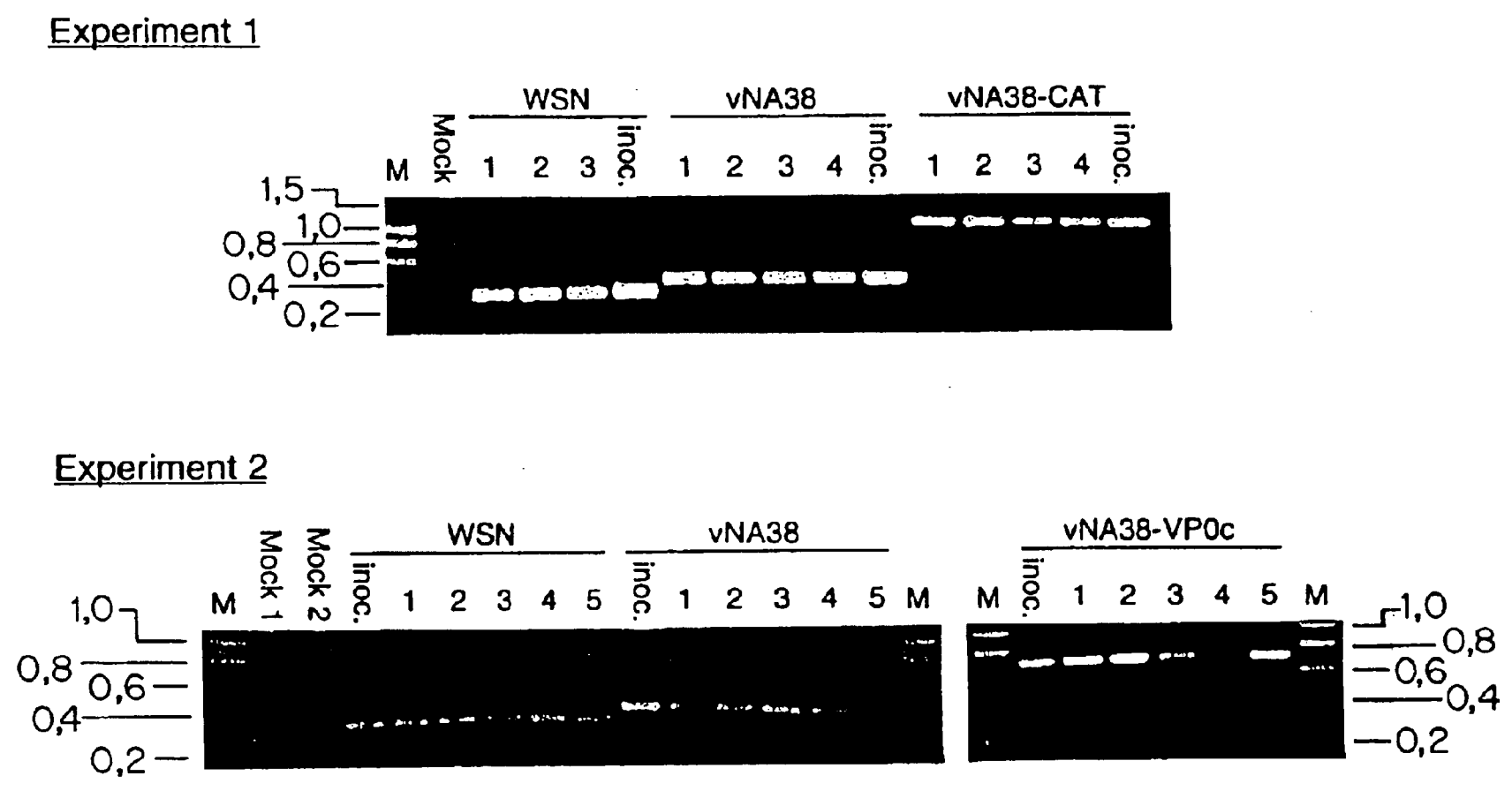

FIG. 9 In vivo genetic stability of the recombinant stability of the recombinant viruses of the vNA38 series. C57BL/6 mice were inoculated intranasally with $10^3$ pfu of wildtype WSN or recombinant vNA38, vNA38-VPOc and vNA38-CAT virus. Four days post challenge infection, mice were sacrificed and lung homogenates were prepared. Viral RNA of the inoculum and of the lung homgeneates were prepared by TRIZOL™extraction and analyzed by RT-CR as described in the FIG. 5 legend.

Figure 10:
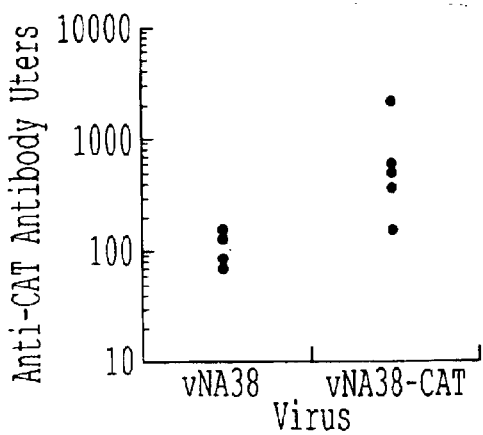

FIG. 10 Anti-CAT antibody response to immunization with vNA38-CAT virus. C57BL/6 mice were inoculated intranasally with $10^3$ pfu of recombinant vNA38 and vNA38-CAT virus. Sera were collected three weeks after the inoculation and the specific anti-CAT response was examined by ELISA, as described in the methods. Titres are represented as the reciprocal of the highest dilution of a given serum, giving an optical density value at 450 nm equal to three times that of background levels.

Figure 11:
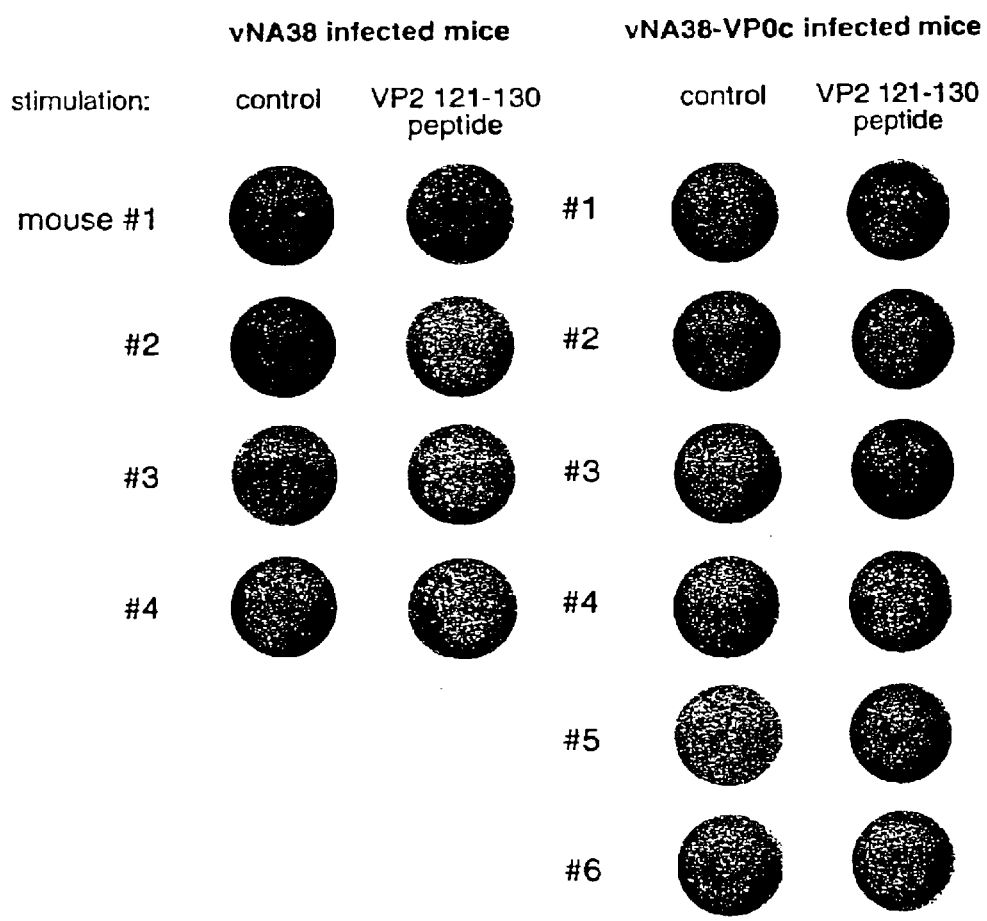

FIG. 11 Induction of a VP0-specific cellular response by immunization with vNA38-VP0c virus. C57BL/6 mice were inoculated intranasaly with $10^3$ pfu of recombinant vNA38 and vNA38-VP0c virus. Splenocytes from infected mice were harvested 2 months after the inoculation and assayed for the presence of Mengo virus-specific CD8+T cells by ELISPOT using the immunodominant VP2 121-130 peptide, as described in the methods.

FIG. 12 Expression of HbsAg by discistronic recombinant RNA molecules and by the vNA38-S virus. For transient expression, subconfluent monolayers of COS-1 cells were transfected by a mixture of plasmids pCDNA-NP, pCDNA-PA, pcDNA-PB1 and pcDNA-PB2 together with any of poll expression plasmid pPRNA38 or pPRNA38-S. For expression after infection, confluent monolayers of COS-1 cells were infected with recombinant or wild-type influenza viruses at an M.O.I. of 5. At 48 hours post-transfection and at 24 and 48 hours post-infection, cell supernatants were collected and assayed for HbsAg levels as described in the methods. Levels are given in ng of HBs antigen per ml of supernatant.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989) and the various references cited therein.

The invention describes the construction and use of recombinant negative strand viral RNA molecules made dicistronic or multicistronic by the use of at least two 3'-non coding flanking sequence of a genomic viral RNA segment. These molecules also comprise 5'-non coding sequences of a genomic viral RNA segment at their 5' end allowing their replication and transcription by viral RNA-dependant RNA polymerase and therefore the expression of viral and/or heterologous gene products in appropriate cells. These RNA molecule may be produced by transfection in animal cells of a plasmid containing appropriate DNA sequences under the control of the polymerase I promoter and upstream of the cDNA of the hepatitis δ ribozyme. Alternatively, these RNA molecules may be prepared by transcription of appropriate DNA sequences using a DNA-dependant RNA polymerase such as bacteriophage T7, T3 or SP6 polymerase.

If the 3'-non coding sequence located at the 3' extremity of the RNA molecule is preceded by the reverse complement of the coding sequence for an authentic, mutated, truncated or chimeric but essential viral protein, such a RNA molecule can be used to rescue a chimeric/recombinant stable and infectious virus, able to propagate in cell culture and/or in animal/human hosts and able to express all the foreign coding sequences wh upstream of the duplicated 3' sequence(s). The dicistronic/multicistronic segment will be maintained in the virus population during passaging, since it is required for the expression of an essential viral protein.

Using influenza virus, for example, it may be preferable to use for 5'- and 3'-non coding sequences any 5'-terminus or 3'-terminus, respectively, of any genome segment of any influenza virus strain. In some cases, mutated 5'- and 3'-non coding sequences may be used. The recombinant negative sense bicistronic/multicistronic RNA molecules may be expressed in appropriate animal cells together with viral RNA-dependant RNA polymerase protein complex (PB1, PB2 and PA) proteins and nucleoprotein: this in vivo reconstituted recombinant RNP complex will allow replication of the recombinant RNA molecule and may be used to express all the encoded heterologous and viral gene products; it may also be used to rescue the recombinant RNA molecule in virus particles by infection of the host cells with an appropriate strain of influenza virus or by coexpression in the host cells of the 6 or 7 other genomic RNA segments necessary to reconstitute a viable influenza virus.

All plasmids (expression vectors) described herein have been obtained by the inventors using techniques known in the art. Their nucleotide sequence is known and available. They have been checked through complete sequencing of the inserts, when these have been obtained through PCR amplification. None of them have been described in any publication except for the pPR7 plasmid which had been previously constructed and described in Crescenzo-Chaigne et al. (Crescenzo-Chaigne, B., N. Naffakh, and S. van der Werf 1999. Comparative analysis of the ability of the polymerase complexes of influenza viruses type A, B and C to assemble into functional RNPs that allow expression and replication of heterotypic model RNA templates in vivo *Virology.* 265:342-53): it allows transcription in primate and human cells of any DNA sequences inserted between the two Bbs 1 restriction site.

pPRNA, pPRNA35 and pPRNA38 series plasmids have been constructed as described in Methods (see below).

The term "expression vector" refers to a polynucleotide which comprises the cDNA sequences of a recombinant RNA molecule or a recombinant vRNA segment of viruses of the present invention. They also provide the sequences necessary for its expression in the selected host cell. Expression vectors will generally include a transcriptional promoter and terminator, or will provide for incorporation adjacent to an endogenous promoter. Expression vectors will usually be plasmids, further comprising an origin of replication and one or more selectable markers.

The use of the recombinant RNAs or viruses of the present invention may be effective in treating or preventing disease caused by disease causing agents. Each disease causing agent or disease state has associated with it an antigen or immunodominant CTL epitope on the antigen or a neutralizing domain on the antigen which is crucial in immune recognition and ultimate elimination or control of the disease causing agent or disease state in a host, sometimes referred to in the art as a protective antigen. The host immune system must come in contact with the antigen or immunodominant epitope on the antigen in order to mount an immune response (CTL or antibody response) against the associated disease causing agent.

The use of recombinant RNAs or viruses of the present invention may comprise one or more nucleic acid sequences encoding one or more isolated antigens or immunodominant CTL epitopes. Such disease causing agents include but are not limited to pathogenic microorganisms. Cancers which may be treated using the recombinant RNAs or viruses of the present invention include but are not limited to primary or metastatic melanoma, thymoma, lymphoma, sarcoma, lung cancer, liver cancer, non-Hodgkins lymphoma, Hodgkins lymphoma, leukemias, uterine cancer, and adenocarcinomas such as breast cancer, prostate cancer, ovarian cancer, pancreatic cancer and the like.

The invention also provides two recombinant viruses vNA38-CAT deposited at the C.N.C.M. on Apr. 12, 2001under the accession number I-2657 and vNA38 deposited at the C.N.C.M. on Apr. 15, 2002 under the accession number I-2848. The address of the C.N.C.M. is Institut Pasteur, 28, rue du Dr Roux, 75724 Paris Cedex 15, France.

These cancers can be assessed or treated by methods described in the present application. In the case of cancer, a gene encoding an antigen associated with the cancer is incorporated into the recombinant RNAs or viruses of the present invention. The antigen associated with the cancer may be expressed on the surface of a cancer cell or may be an internal antigen.

Genes encoding an antigen of a disease causing agent in which the agent is a pathogenic microorganism include viruses such as HIV (GP-120, p17, GP-160 antigens), influenza (NP, HA antigen), herpes simplex (HSVdD antigen), human papilloma virus, equine encephalitis virus, hepatitis (Hep B Surface Antigen) and the like. Pathogenic bacteria include but are not limited to Chlamydia, Mycobacteria, Legioniella and the like. Pathogenic protozoans include but are not limited to malaria, Babesia, Schistosomiasis and the like. Pathogenic yeast include Aspergillus, invasive Candida, and the like.

Immunostimulatory agents or adjuvants have been used to improve the host immune responses to, for example, vaccines. Thus, adjuvants have been identified that enhance the immune response to antigens. Some of these adjuvants are toxic, however, and can cause undesirable side-effects, making them unsuitable for use in humans and many animals. Aluminum hydroxide and aluminum phosphate are commonly used as adjuvants in human and veterinary vaccines.

Other extrinsic adjuvants and other immunomodulating materials can elicit immune responses to antigens. These include saponins complexed to membrane protein antigens to produce immune stimulating complexes (ISCOMS), pluronic polymers with mineral oil, killed mycobacteria in mineral oil, Freund's complete adjuvant, bacterial products, such as muramyl dipeptide (MDP) and lipopolysaccharide (LPS), as well as monophoryl lipid A, QS 21 and polyphosphazene.

The term "unit dose" as it pertains to the inoculum refers to physically discrete units suitable as unitary dosages for mammals, each unit containing a predetermined quantity of the recombinant RNA or viruses calculated to produce the desired immunogenic effect in association with the required diluent. The specifications for the novel unit dose of an inoculum of this invention are dictated by and are dependent upon the unique characteristics of the recombinants and the particular immunologic effect to be achieved.

The inoculum is typically prepared as a solution in tolerable (acceptable) diluent such as saline, phosphate-buffered saline or other physiologically tolerable diluent and the like to form an aqueous pharmaceutical composition.

The route of inoculation may be intravenous, intramuscular, subcutaneous, intradermal, intranasal, oral and the like, which results in eliciting a protective response against the disease causing agent. The dose is administered at least once. Subsequent doses may be administered as indicated.

In providing a mammal with the recombinants of the present invention, preferably a human, the dosage of administered recombinant virus will vary depending upon such factors as the mammal's age, weight, height, sex, general medical condition, previous medical history, disease progression, tumor burden and the like.

One skilled in the art would know the conventional methods to assess the aforementioned parameters.

Included within the scope of the present invention are pharmaceutical compositions containing one or more of the recombinant RNAs and/or viruses. Such pharmaceutical compositions also contain one or more conventionally pharmaceutically acceptable ingredients, carriers, diluents, etc.

According to the present invention foreign sequences encoding antigenic determinants of any pathogens, such as bacteria, viruses or parasites may be expressed. Either a live recombinant vaccine or an inactivated recombinant vaccine can be formulated with such a chimeric influenza virus and can be used as vaccines against such pathogens. In the case of a live recombinant vaccine, the ability of influenza virus to induce a strong secretory and cellular immune response is an advantageous property. In this regard, the use of attenuated influenza virus strains such as the cold adapted strains which have been evaluated under phase III clinical trials in humans (Mendelman, P. M., J. Cordova, and I. Cho 2001. Safety, efficacy and effectiveness of the influenza virus vaccine, trivalent, types A and B, live, cold-adapted (CAIV-T) in healthy children and healthy adults *Vaccine*. 19:2221-2226) would have to be considered. For inactivated vaccine, the heterologous gene product could be expressed so as to be expressed in association with the virion: this may be achieved, for example, by fusing the heterologous sequence to those of the transmembrane and cytosolic part of the HA, NA or M2 viral product. This would allow copurification of the heterologous product with the viral particle and/or likely enhance its immunogenicity.

In another embodiment of the invention, any biologically active protein can be expressed. For example, a chimeric influenza virus able to express an immunomodulatory cytokine could be more immunogenic or more attenuated in its natural host. It could thus be used as a more effective or safer live attenuated vaccine against influenza. It could also be used to modulate the immune response against any other pathogens or any pathogens infecting the respiratory tract. As another example, an attenuated chimeric influenza virus could allow the transient expression of a therapeutic protein in the respiratory tract of infected hosts.

In another embodiment, any reporter gene may also be expressed. Such a chimeric influenza virus, if used as a live attenuated vaccine against influenza, would allow discrimination between natural infection and vaccination of the host, because only the vaccinated host would have an immune response (e.g. circulating antibodies) against the reporter protein.

Having generally described this invention, a further understanding can be obtained by reference to certain specific examples which are provided herein for purposes of illustration only, and are not intended to be limiting unless otherwise specified.

EXAMPLES

Methods

Cells and Viruses.

MDBK (Madin Darby bovine kidney) and MDCK (Madin Darby canine kidney) cells were grown at 37° C. under 5% $CO_2$ in DMEM complete medium [Dulbecco's modified Eagle medium with 1 mM sodium pyruvate, 4.5 mg/ml L-glucose, 100 U/ml penicillin and 100 µg/ml streptomycin], supplemented with 5% heat-inactivated foetal calf serum (FCS) (TechGen). COS-1 cells were grown in DMEM complete medium but 10% FCS.

Influenza virus A/WSN/33 (WSN, H1N1) and the WSN/HK (H1N2) reassortant were kindly provided by Dr Peter Palese (Mount Sinaï School of Medicine, New York, USA). Viral stocks were produced by serial allantoic passage on 11 day-old embryonated hen's eggs.

Construction of polymerase I (pol I) expression plasmids (transfer plasmids) for reverse genetics.

For construction of transfer plasmids, cDNA (in negative polarity) corresponding to wild-type or recombinant NA segment of the WSN influenza virus were cloned into the pol I expression plasmid pPR7, which contains a truncated human RNA polymerase I promoter and the hepatitis δ virus ribozyme and allows the synthesis of a viral RNA-like transcript in transfected cells (Crescenzo-Chaigne, B., N. Naffakh, and S. van der Werf 1999. Comparative analysis of the ability of the polymerase complexes of influenza viruses type A, B and C to assemble into functional RNPs that allow expression and replication of heterotypic model RNA templates in vivo *Virology*. 265:342-53).

Briefly, the entire NA segment cDNA was amplified by PCR with the PWO polymerase (Roche) using plasmid pT3NAM1 (kindly provided by Dr Peter Palese, and described in Garcia Sakie et al (1994) Journal of Virology 68:6254-6261) as a template and oligonucleotides 5'-AGCAAAAGCAGGAGTTTAAATG-3' (SEQ ID NO: 3) and 5'-AGTAGAAACAAGGAGTTTTTTGAAC-3' (SEQ ID NO: 4). The pPRNA plasmid was obtained by the insertion of the resulting DNA fragment between the two Klenow-treated BbsI sites of plasmid pPR7 and the sequencing of positive clones using a Big Dye terminator sequencing kit and an ABI377 automated sequencer (Perkin-Elmer).

The pPRNA35 plasmid was constructed in two steps. First, a recombinant viral cDNA fragment was generated by PCR with Expand High Fidelity polymerase mix (Roche) using plasmid pT3NAM1 as a template and oligonucleotides 5'AGCAAAAGCAGGAGTTTAAATG-3' (SEQ ID NO: 5) and 5'-AGTAGAAACAAGGAGTTTTTTGAACAAAG-CTAGCTCTCGAGTTAAACTCCTGCTTTTGCTAGAT-CTACTTGTCAATGGTGAACGGCAACTCAGC-3' (SEQ ID NO: 6) and was inserted at the Hind II site of pUC19 plasmid, yielding plasmid pUCNA35. The resulting plasmid was used as the template for a second PCR reaction with the oligonucleotides 5'-GACGGTCTCTGG-CCAGCAAAAGCAGGAGTTTAAATGAATC-3' (SEQ ID NO: 7) and 5'-GACGGTCTCATATTAGTAGAAAC-AAGGAGTTTTTTGAACA-3' (SEQ ID NO: 8), which included a Bsa I restriction enzyme site (underlined). The amplified product was digested with Bsa I then cloned between the two BbsI sites of plasmid pPR7, yielding plasmid pPRNA35. Positive clones were sequenced as indicated above. This plasmid contains a recombinant NA segment cDNA, where the NA ORF is followed by a duplicated 3' promoter, an Xho I/Nhe I linker and the original 5' promoter.

For cloning purposes, the coding sequences of the Chloramphenicol Acetyl Transferase (CAT) and Green Fluorescent Protein (GFP) as well as the VP0c fragment (aa 157-249) of the Mengo virus VP0 polypeptide were amplified by PCR using respectively the oligonucleotides 5'-GACCTCGAGCATGGAGAAAAAAATCACTGGGTA- TAC-3 '(SEQ ID NO: 9) and 5'-CAGGCTAGCTACGC-CCCGCCCTGCCACTCA-3' (SEQ ID NO: 10) with plasmid pPOL1-CAT-RT (Pleschika et al (1996) Journal of Virology 70:4188-4192) as a template, oligonucleotides 5'-GACCTCGAGCATGGTGAGCAAGGGCGAGGAG-3' (SEQ ID NO: 11) and 5'-CAGGCTAGCTACTTGTACA-GCTCGTCCATGCC-3' (SEQ ID NO: 12) with plasmid pEGFP-N1 (Clontech) and oligonucleotides 5'-GACCTC-GAGCATGGGACATCATCATCATCATCATGTTCTATC-AGGTGAGGAT GGTGGTGTC-3' (SEQ ID NO: 13) and 5'-CAGGCTAGCTACGGATAGAGAGTCCATT-GCCAAAAA-3' (SEQ ID NO: 14) with plasmid pM16.1 (Duke, G. M., and A. C. Palmenberg 1989. Cloning and synthesis of infectious cardiovirus RNAs containing short, discrete Poly(C) tracts *Journal of Virology.* 63:1822-1826). The oligonucleotides were designed so that the resulting DNA fragments included a Xho I site before the initiation codon and a Nhe I site after the termination codon, and, for the VP0c fragment, a stretch of 6 histidines after the initiating methionine. They were cloned between the AXho I and Nhe I site of plasmid pPRNA35, yielding respectively plasmid pPRNA35-CAT, pPRNA35-GFP and pPRNA35-VP0c. Positive clones were sequenced as indicated above.

The pPRNA37, pPRNA37-CAT and pPRNA37-GFP plasmid were obtained by removing the internal 3' viral promoter from plasmid pPRNA35, pPRNA35-CAT and pPRNA35-GFP respectively, by digestion with Bgl II and Xho I, klenow filling and ligation. The coding sequences of the VP0c polypeptides were inserted into the pPRNA37 plasmid in the same manner as for the pPRNA35 plasmid (see above), yielding plasmid pPRNA37-VP0c.

The pPRNA3 8 plasmid was constructed by inserting into the Nhe I- and Hind III-digested pPRNA35 plasmid a DNA fragment which was obtained by PCR amplification of plasmid pPRNA using the oligonucleotides 5'-GACGCTAGCTGGCCAGACGGTGCTGAGTTGCC-GTTC-3' (SEQ ID NO : 15) and 5'-GTGAGCGGATAA-CAATTTCACAC-3' (SEQ ID NO: 16) followed by digestion with Nhe I and Hind III. This plasmid contains a recombinant NA segment cDNA, where the NA ORF is followed by a duplicated 3' promoter, an Xho I/Nhe I linker, a duplication of the last 39 nucleotides plus termination codon of the NA ORF and the original 5' promoter.

The coding sequences of the CAT, GFP and VP0c polypeptides were inserted into the pPRNA38 plasmid in the same manner as for the pPRNA35 plasmid (see above), to give rise to plasmids pPRNA38-CAT, pPRNA38-GFP and pPRNA38-VP0c respectively.

For construction of the pPRNA38-S plasmid, the coding sequences of the major envelope protein (S) of the Hepatitis B surface antigen (HbsAg) were amplified by PCR using the oligonucleotides 5'-GACCTCGAGAACATGGAGAACA-TCACATCAGG-3' (SEQ ID NO: 17) and 5'-CAGGCTA-GCTAAATGTATACCCAAAGACAAAAGAA-3' (SEQ ID NO: 18) with plasmid pCMV-S2.S (Michel et al (1995) Proc. Natl. Acad. Sci. USA 92:5307-5311) as a template and, the resulting DNA fragments were cloned between the XhoI and NheI sites of plasmid pPRNA38. Positive clones were sequenced as indicated above.

Reverse genetics of the recombinant viruses

The procedures used for the reverse genetics of the recombinant influenza viruses were performed as described previously by Pleschka et al. ( Pleschka, S., R. Jaskunas, O. G. Engelhardt, T. Zurcher, P. Palese, and A. Garcia-Sastre 1996. A plasmid-based reverse genetics system for influenza A virus *Journal of Virology.* 70:4188-92.). Briefly, any of the purified pol I transfer plasmid (1 µg) was transfected into a subconfluent monolayer of COS-1 cells (3×105 cells in 35 mm dishes) together with plasmids pcDNA-NP (2 µg), pcDNA-PA (1 µg), pcDNA-PB 1 (1 µg) and pcDNA-PB2 (1 µg) by using 10 µl of Fugene™6 reagent (Roche) according to the manufacturer's recommandations. pcDNA plasmids were kindly provided by Dr Ervin Fodor (University of Oxford, Oxford, UK). Alternatively, in some experiments, the pcDNA plasmids were replaced by the pHMG-NP, pHMG-PA, pHMG-PB1 and pHMG-PB2 plasmids, which were kindly provided by Dr J. Pavlovic (Institute fur Medizinische Virologie, Zurich, Switzerland). After 24 hours of incubation at 35° C., the cells were infected at an M.O.I. of 1 with the WSN/HK helper virus and incubated at 35° C. for 2 more days in complete DMEM but 2% FCS. The recovered viruses were amplified once on MDCK cells, plaque purified twice on MDBK cells before final amplification on MDBK cells (viral stock p1). Under these conditions, only transfectant viruses containing a NA RNA segment with WSN sequences were rescued; viruses containing the NA RNA segment of WSN/HK (H1N2) helper virus are not able to grow on MDBK cells (Schulman, J. L., and P. Palese 1977. Virulence factors of influenza A viruses: WSN virus neuraminidase required for plaque production in MDBK cells *Journal of Virology.* 24:170-6). Subsequent passages of the recombinant viruses were performed at an M.O.I of 0.01 on MDCK cells for 3 days at 35° C. in DMEM complete medium but 2% FCS. All viral stock were titered on MDCK cell monolayers, in a standard plaque assay using an agarose overlay in DMEM complete medium but 2% FCS.

Analysis of CAT expression in transfected or infected cells

For the transient expression assay, subconfluent monolayers of COS-1 cells ( $3 \times 10^5$ cells in 35 mm dishes) were transfected using the Fugene™6 mediated method (Roche) by a mixture of plasmids pcDNA-NP, pcDNA-PA, pcDNA-PB1 and pcDNA-PB2 (2, 1, 1, 1 µg) together with 1 µg of pol I expression plasmid pPRNA35-CAT, pPRNA37-CAT or pPRNA38-CAT. Cells were incubated at 35° C. in DMEM complete medium. At 48 hours post-transfection, cell extracts were prepared in 500 µl of lysis buffer and tested for CAT levels using the CAT ELISA kit (Roche) which allowed detection of 0.05 ng/ml CAT.

Alternatively, confluent monolayers of COS-1 or MDCK cells were infected with recombinant or wild-type influenza viruses at an M.O.I of 2. 8 and 24 hours after infection, cell extracts were prepared and assayed for CAT levels as described above.

Analysis of HbsAg expression in transfected or infected cells

For the transient expression assay, subconfluent monolayers of COS-1 cells ($3 \times 10^5$ cells in 35 mm dishes) were transfected using the FUGENE 6™ mediated method (Roche) by a mixture of plasmids pcDNA-NP, pcDNA-PA, pcDNA-PB1 and pcDNA-PB2 (2, 1, 1, 1 µg) together with 1 µg of pol I expression plasmid pPRNA38-S or, as a control, pPRNA38. Cells were incubated at 35° C. in DMEM complete medium. At 48 hours post-transfection, cell supernatants were colleceted clarified by low speed centrifugation (5 minutes at 3000 g) and assayed for HbsAg levels using the Monolisa kit (BioRad).

Confluent monolayers of COS-1 or MDCK cells were infected with recombinant or wild-type influenza viruses at an M.O.I. of 5. 24 and 48 hours after infection, cell supernatants were collected and assayed for HbsAg levels as described above.

Immunizations

C57BL/6 male mice (IFFA CREDO), 7 to 8 weeks of age, were lightly anaesthetized with 100 mg/kg of ketamine (Merial) and inoculated intranasally with $10^3$ pfu of recombinant or wildtype WSN virus in 40 µl of PBS.

Blood from mice was collected three weeks after the inoculation. Serial dilutions of serum samples were used to determine CAT-specific antibody titres by ELISA using CAT protein as antigen. Briefly, 96-well ELISA plates (NUNC Maxisorp) were coated with 0.25 µg of purified CAT protein (Sigma) per well in 0.2 M Na-carbonate buffer, pH 9.6 (overnight at 4° C.). Bound antibody was detected with a 1/1000 dilution of antimouse IgG(H+L) sheep antibody carrying the Horseradish Peroxidase (Amersham) and revealed by the addition of TMB peroxidase substrate (KPL) as indicated by the supplier. Titiers are calculated as the reciprocal of the dilution of serum, for a given mouse, giving an optical density value at 450 nm equal to three times that of background levels.

Spleen cells were collected three weeks after the last inoculation and analyzed for the presence of Mengo virus specific CD8+T cells in a standard ELISPOT assay system. Briefly, $10^6$ spleen cells were stimulated for 20 hours with 1 µg VP2 121-130 synthetic peptide (FHAGSLLVFM, Neosystem) and IL2 (10U/ml) in the presence of $5\times10^5$ irradiated (2000 rads) syngeneic spleen cells per well as feeder cells in 96-wells Multiscreen HA nitrocellulose plates (Millipore), which had been coated with rat-antimouse IFN-γ antibodies (R4-6A2, Becton-Dickinson). Spots were revealed by successive incubations with biotinylated anti-mouse IFN-γ antibodies (xMG1,2-Becton-Dickinson) alkaline phosphatase-conjugated strepavidin (Becton-Dickinson) and BCIP/NBT substrate (Sigma).

Analysis of NA expression in transfected or infected cells

MDCK cells grown in 35-mm dishes were infected with either recombinant or wild-type WSN viruses at an M.O.I of 2. COS-1 cells were transfected as described in the preceding section. 8 hours after infection or 48 hours after transfection, cells were detached using the Cell Dissociation Solution (SIGMA) and incubated for 30 minutes at 4° C. in 100 µl of PBS-BSA (PBS with 0,02% sodium azide and 1% bovine serum albumin) containing 1:1000 dilution of the mouse monoclonal antibody 10C9, which is specific for the WSN-NA protein (kindly provided by Dr Peter Palese). After two washes in PBS-0,02% azide, the cells were incubated for 30 minutes at 4° C. in 100 µl of PBS-BSA BSA containing 10 µg/ml of FITC-conjugated anti-mouse IgG antibodies (Becton-Dickinson). Finally, cells were washed twice in PBS, fixed with 100 µl of PBS, 1% paraformaldehyde and analyzed for fluorescence intensity on a FACS-calibur fluorocytometer (Becton-Dickinson).

Northern Blot analysis

COS-1 cells grown in 35-mm dishes were (a) infected with either recombinant or wild-type WSN viruses at an M.O.I of 2 or (b) transfected using the Fugene™6 mediated method (Roche) as described above. 22 hours post-infection or 48 hours post-transfection, cells were washed twice in PBS and total cellular RNAs were isolated by Trizol™ extraction (Life Technologies) according to the manufacturer's recommendations, followed by digestion with 8 units of DNase I (Ambion) in 60 µl of 10 mM Tris-HCl pH7.5, 2.5 mM $MgCl_2$, 0.1 mM $CaCl_2$ for 60 minutes at 37° C., phenol extraction and isopropanol precipitation.

After denaturation, samples (3 µg) were run on an 1% agarose-formaldehyde gel, blotted onto a nylon membrane (Hybond N, Amersham), and hybridized with a CAT-specific $^{32}$p labeled riboprobe allowing the detection of either the negative stranded (vRNAs) or positive stranded (cRNAs, mRNAs) RNAs. Hybridizations were performed at 65° C. in a solution containing 50% formamide, 5×SSC, 5× Denhardt solution and 0.5% SDS. The membranes were washed 3 times in a 2×SSC, 0.1%SDS solution at room temperature and another 3 times in a 0.1×SSC, 0.1% SDS solution at 75° C. Finally the membranes were exposed on a STORM™820 phosphorimager (Molecular Dynamics) and analysed using the Image Quant program (Molecular Dynamics).

EXAMPLES

Dicistronic negative sense RNA molecules were engineered from the NA segment of influenza virus A/WSN/33 (WSN) virus.

The first NA35 series of dicistronic RNA molecules were constructed as described in methods. The cDNA of these molecules have been cloned, in negative sense orientation, in plasmid pPR7 downstream of the truncated human RNA polymerase I promoter and upstream of the ribozyme sequence of the hepatitis γ virus. Transfection of such plasmids in appropriate cells, such as the primate COS-1 cells, allows the synthesis of a viral RNA-like transcript. As an example, plasmid pPRNA35-CAT encodes a dicistronic recombinant NA segment cDNA molecule in which the NA ORF of WSN virus, in negative sense orientation, is placed upstream of the 19 3' terminal nucleotides of the WSN genomic segment 6 (NA segment) and downstream of the 28 5' terminal nucleotides of the WSN genomic segment 6, the ORF of the CAT gene flanked by Xho I and Nhe I restriction site, in negative sense orientation, and a duplication of the 19 3' terminal nucleotides of the WSN genomic segment 6.

Figure 1:
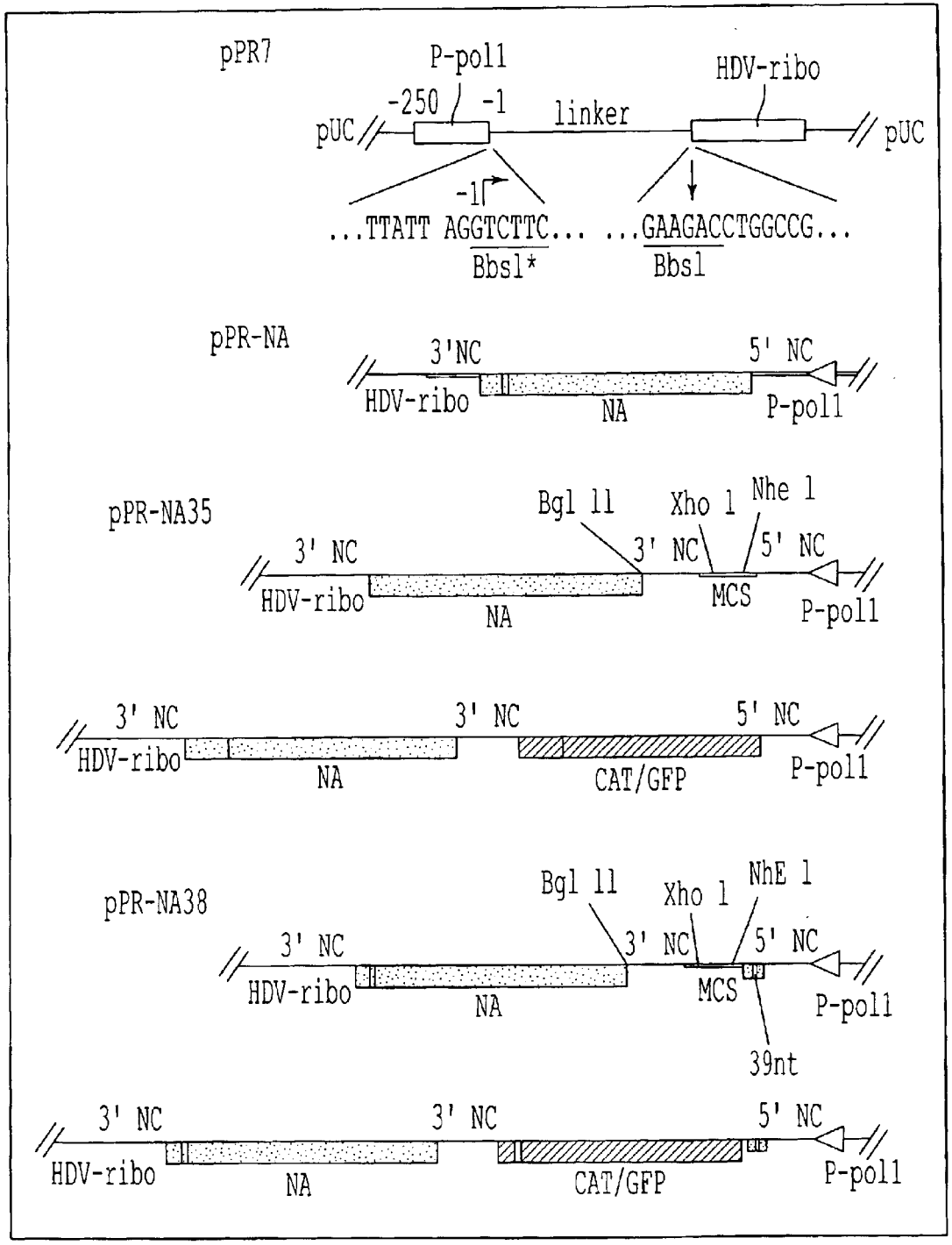
FIG. 1: Schematic representation of the transfer plasmids, the positions of the BbsI restriction enzyme sites are shown (SEQ ID NOS: 1 and 2).
Figure 2:
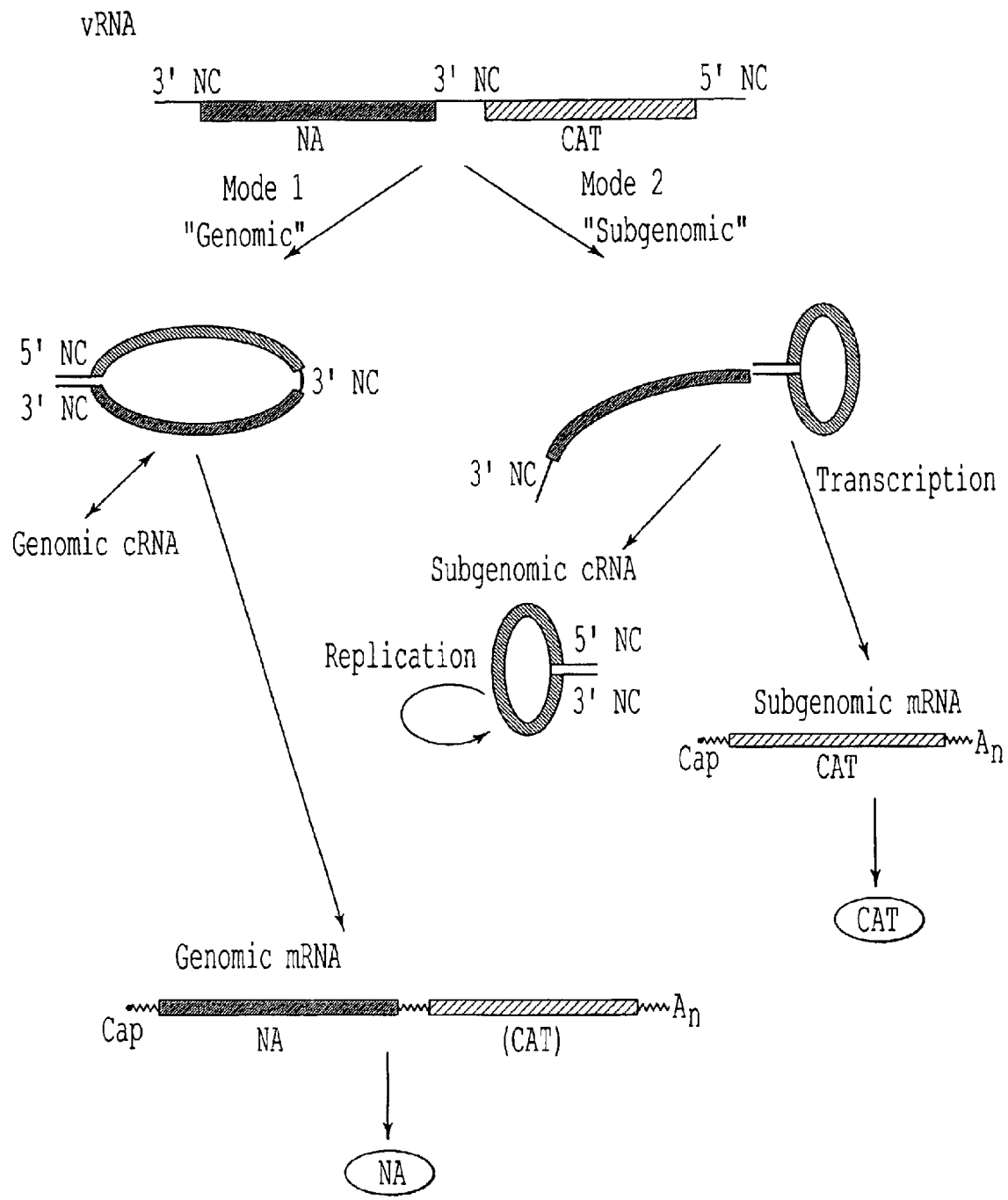
FIG. 2: the two replication modes of a recombinant influenza vRNA segment (NA35-CAT), which was made dicistronic by the duplication of its 3'-terminus and the insertion of a foreign gene ORF, in negative sense orientation.
Figure 3A:
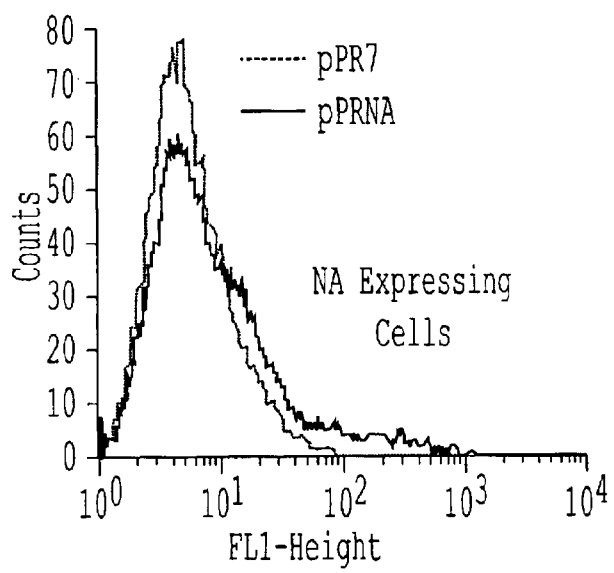
FIG. 3: Transient expression of the two cistrons by the recombinant dicistronic NA3 5-CAT RNA molecule. COS-1 cells were transfected as described in methods with the four polII expression plasmids pcDNA-NP, pcDNA-PA, pcDNA-PB 1 and pcDNA-PB2 together with one of the following plasmid: pPR7, pPRNA35, pPRNA35-CAT, pPRNA37, pPRNA37-CAT, pPRNA38 or pPRNA38-CAT.
Figure 3A:
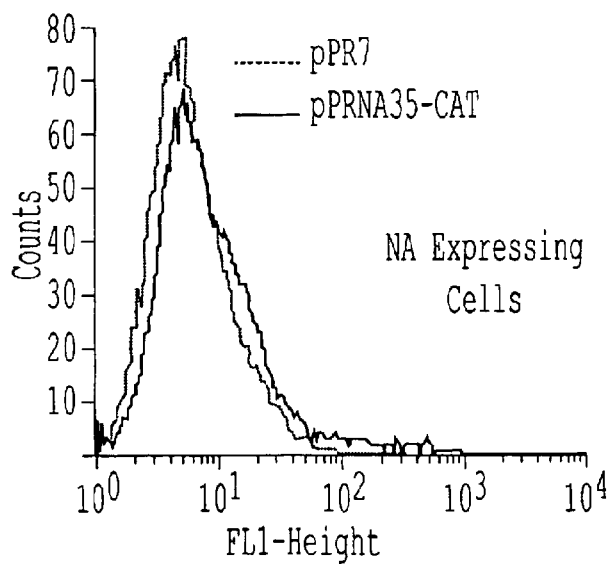

Use of dicistronic recombinant RNA molecule for transient expression When COS-1 cells were cotransfected by the pPRNA35-CAT plasmid together with the four polII expression plasmids pcDNA-PB1, pcDNA-PB2, pcDNA-PA and pcDNA-NP, CAT activity (FIG. 3a) and NA expression could be detected (FIG. 3b). This result suggested that the NA35-CAT dicistronic RNA molecule was replicated and transcribed by the influenza RNA polymerase complex in two modes, as depicted in FIG. 2:

a genomic mode, after interaction of the single 5'-non coding sequence (5' terminal nucleotides, 5' promoter) with the distal 3'-non coding sequence (3' terminal nucleotides, 3' promoter). This mode allows replication of the full length dicistronic RNA molecule, the transcription of a full length mRNA and therefore expression of the NA gene product.

a subgenomic mode, after interaction of the 5' promoter with the duplicated internal 3' promoter. This mode allows replication of a subgenomic RNA molecule in which the CAT ORF sequences, in negative sense orientation, are flanked by the 5' and 3' promoter, the transcription of a subgenomic mRNA and therefore expression of the CAT gene product.

Figure 3C:
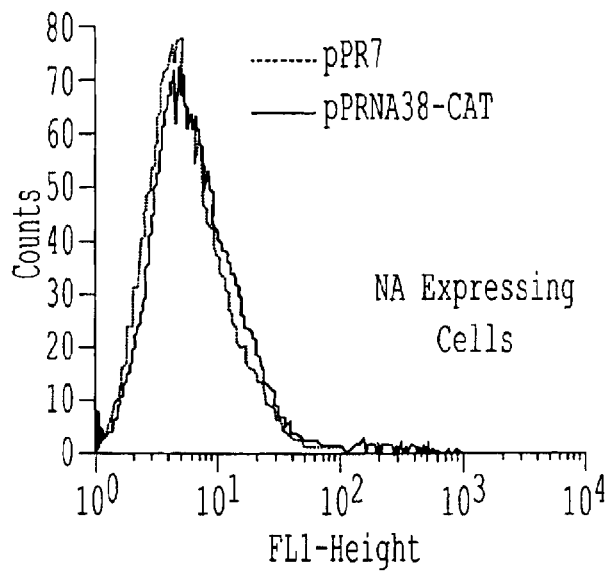
Figure 3C:
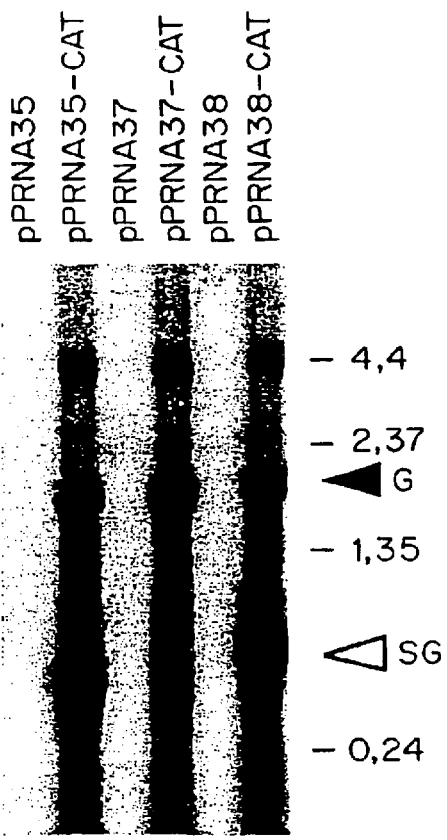

To further demonstrate the existence of 2 modes of replication of the dicistronic recombinant RNA molecules Northern Blot analysis was performed on total RNA extracted from COS-1 cells, which were cotransfected by the pPRNA35-CAT plasmid together with the four polII expression plasmid pcDNA-PB1, pcDNA-PB2, pcDNA-PA and pcDNA-NP. After hybridization to a positive sense riboprobe, specific for CAT sequence, two RNA species could be detected (FIG. 3c); they corresponded in size to the full length genomic vRNA-like molecule (negative polarity) and the shorter subgenomic vRNA-like molecule (negative polarity). Similar analyses performed with a negative sense riboprobe allowed the detection of full-length genomic complementary RNA (cRNA, positive polarity) and mRNA and shorter subgenomic cRNA and mRNA (data not shown).

Use of dicistronic recombinant RNA molecule for rescuing stable and infectious influenza viruses with a dicistronic genomic segment Using the methodology described above, the inventors also demonstrated the rescue of the dicistronic recombinant NA35-CAT RNA molecule into stable and infectious influenza viruses. Practically, COS-1 cells were cotransfected by the pPRNA35-CAT plasmids together with the four polII expression plasmid pcDNA-PB1, pcDNA-PB2, pcDNA-PA and pcDNA-NP, as described above. When the COS-1 cells were superinfected with the WSN/HK influenza virus lacking the WSN NA gene, release of viruses containing the recombinant NA35-CAT RNA molecule occured. These viruses, named vNA35-CAT, were plaque purified on MDBK cells, titered on MDCK cells (FIG. 4) and analyzed for their phenotype and genotype.

PCR analysis of the NA segment of the parental WSN virus, recombinant vNA35 and vNA35-CAT viruses, performed as described in FIG. 5, together with sequencing of the amplified product, demonstrated the presence in the recombinant viruses of the expected dicistronic RNA segment. Viability and genotype of the recombinant virus demonstrated that the viral polymerase complex expressed by influenza virus infection was able to replicate and transcribe the recombinant dicistronic RNA in the genomic mode, which allows propagation of the genetic information of the recombinant virus together with expression of the viral NA gene product.

Infection of COS-1 cells with recombinant vNA3 5-CAT viruses allowed the detection of CAT activity (FIG. 6), which suggested that the viral polymerase complex expressed by influenza virus infection was able to replicate and transcribe the recombinant dicistronic RNA segment in the subgenomic mode together with expression of the foreign coding sequence.

As for the transient expression assays (see above), this was further demonstrated by Northern Blot analysis performed on total RNA extracted from COS-1 cells, which were infected with recombinant vNA35 and vNA35-CAT viruses. After hybridization to a positive sense riboprobe, specific for CAT sequence, two RNA speciescould be detected; they corresponded in size to the full length genomic vRNA-like molecule (negative polarity) and the shorter subgenomic vRNA-like molecule (negative polarity). Similar analyses performed with a negative sense riboprobe allowed the detection of full-length genomic complementary RNA (cRNA, positive polarity) and mRNA and shorter subgenomic cRNA and mRNA (data not shown). NA38 series of recombinant RNA molecules The second NA3 8 series of recombinant dicistronic RNA molecules were constructed as described in the methods. These molecules contain a duplication of the 39 last nucleotides plus termination codon of NA ORF, which extended the 5' terminus of the recombinant vRNA molecule from the 28 nt of the 5' non coding region itself to the 70 first nucleotides of the 5' terminus of the original NA segment of virus WSN. As for the NA35 series, they were also rescued into stable and infectious recombinant influenza viruses using the methodology described above.

NA38-CAT recombinant RNA molecules replicated to the same extent and expressed similar quantities of CAT gene product than NA35-CAT molecules after transient expression in COS-1 cells when a functional RNA polymerase complex was provided by co-transfection of the four polII expression plasmid pcDNA-PB1, pcDNA-PB2, pcDNA-PA and pcDNA-NP (FIG. 3).

In contrast, vNA38-CAT recombinant viruses replicated to higher titers in MDCK cells (FIG. 8), gave larger plaques (FIG. 4) and expressed much higher levels of CAT gene product (FIG. 6) than did vNA35-CAT recombinant viruses. This was correlated to the higher levels of genomic NA segment vRNA (segment 6) and subgenomic recombinant vRNA-like molecules in COS-1 cells infected with the NA3 8-CAT viruses than with the vNA35-CAT viruses (FIG. 7).

Genetic stability of the dicistronic NA segment of the recombinant vNA3 8, vNA38-CAT and vNA38$_{13\ VP0c}$ was assayed by RT-PCR analysis. Together with sequencing of the amplified product, as described in FIG. 5. This demonstrated that these recombinant viruses harbored the expected dicistronic RNA segment in a stable manner. Furthermore, in vivo genetic stability was analyzed in C57BL/6 mice which had been infected by recombinant viruses of the vNA38 series. As shown in FIG. 9, vNA38-CAT and vNA38VP0c retained the foreign sequences upon multiplication in the lungs of infected mice.

An additional DNA band can be noticed in PCR amplification products obtained from NA38 type viruses. Altough this DNA band migrates with the same size as the PCR product amplified from the wt NA gene, it does not indicate genotypic reversion of NA38 type viruses towards wt genotype. According to our analysis, it is a PCR artefact, because:

this additional band is present in PCR amplification from all NA38 type plasmid DNA(T+)

its intensity does not increase during propagation of NA3 8 type viruses its intensity is strictly correlated to the intensity of the expected band the phenotype of NA38 type viruses does not evolve towards a wild type phenotype (large plaques) during viral propagation Induction of CAT specific antibodies after immunization of mice with recombinant virus vNA38-CAT In order to establish the feasibility of using dicistronic influenza viruses for eliciting a heterospecific immune response, the inventors determined whether recombinant vNA38-CAT virus inoculated as live virus was able to induce in mice specific antibodies directed against the CAT protein.

To this end, C57BL/6 mice were inoculated intranasally with $10^3$ pfu of recombinant vNA38-CAT virus or with parental vNA38 virus as a control. Sera were collected three weeks after the inoculation and the specific anti-CAT response was examined by ELISA, as described herein. As shown in FIG. 10, one inoculation of live vNA38-CAT virus induced serum antibodies against the CAT proteins Induction of a Mengo virus specific, class I restricted CD8+ cellular response after immunization of mice with recombinant virus vNA38-VP0c In order to evaluate whether recombinant vNA38-VP0c virus inoculated as a live virus was able to induce a specific CD8+T cell response directed against Mengo virus antigens, C57BL/6 mice were inoculated intranasally with $10^3$ pfu of recombinant vNA38-VP0c virus or with parental vNA38 virus as a control.

Splenocytes from infected mice were harvested 3 weeks after the inoculation and assayed for the presence of Mengo virus specific CD8+T cells by ELISPOT after stimulation with the immunodominant VP2 121-130 peptide, as described herein. As shown in FIG. 11, spots were detected from spleen cell cultures initiated from mice infected with vNA38-VP0c. No or much fewer spots were observed with splenocytes from mice that were infected with control vNA38 virus or with splenocytes cultivated in the absence of the VP2 peptide (background levels). These findings showed that the dicistronic vNA38-VP0c influenza virus induced class I-restricted T lymphocytes specific for the Mengo virus VP2 121-130 peptide.

Taken together, the last two examples demonstrate that dicistronic influenza viruses of the vNA38 series are able to induce both humoral (antibodies) and cellular immune responses against encoded heterologous proteins.

Dicistronic recombinant influenza viruses can express the Hepatitis B surface Antigen (HbsAg)

In order to evaluate whether dicistronic recombinant RNA molecules or dicistronic influenza viruses could express an antigenic determinant of a foreign pathogen, the authors constructed the NA38-S dicistronic RNA molecule. This molecule encodes the major protein (S) of the surface antigen of Hepatitis B virus (HbsAg). Next, using the transient expression assay described herein, HbsAg secretion was detected in the supernatant of transfected COS-1 cells (FIG. 12). This indicated that the recombinant NA38-S molecule was replicated and transcribed by the influenza RNA polymerase complex as was the case for the NA38-CAT molecule described above.

The NA38-S molecule was also rescued into a stable and infectious recombinant influenza virus (vNA38-S) using the reverse genetics methodology described herein. The vNA38-S virus replicated to high titers in MDCK cells, gave medium sized plaques on MDCK cells (data not shown) and permitted the synthesis and secretion of HbsAg in infected COS cells (FIG. 12).

Obviously, numerous modifications and variations on the present invention are possible in light of the above teachings. It is therefore to be understood that within the scope of the appended claims, the invention may be practiced otherwise than as specifically described herein.

What is claimed is:

1. A recombinant RNA molecule comprising, from the 3' end to the 5' end:
   a) at least two units, each of them composed of a wild-type, truncated or mutated 3'-non coding flanking sequence of a genomic RNA segment of a segmented negative strand RNA virus, optionaly a given spacer sequence of a size choosen from 0 nucleotide to 500 nucleotides, the reverse complement of an mRNA coding sequence or of a fragment of an mRNA coding sequence linked in frame to an initiating AUG and termination codon, a second spacer sequence of a size choosen from 0 nucleotide to 500 nucleotides; and
   b) a wild-type, truncated or mutated 5'-non coding flanking sequence of a genomic RNA segment of a segmented negative strand RNA virus.

2. A recombinant RNA molecule according to claim 1, wherein the spacer sequence of step a) has preferably a size choosen from 15 to 150 nucleotides.

3. The recombinant RNA molecule of claims 1 or 2, wherein the first unit, located at the 3' extremity of the RNA molecule, comprises the reverse complement of the coding sequence selected from the group consisting of a nonmutated viral protein, a mutated viral protein, a truncated viral protein, and a chimeric viral protein for an authentic, mutated, truncated or chimeric viral protein.

4. A recombinant virus comprising a segmented negative strand virus, in which at least one genomic segment has been substituted with the recombinant RNA molecule according to claims 1 to 3.

5. The recombinant virus according to claim 4, wherein the first unit, located at the 3' extremity of the recombinant RNA segment contains the reverse complement of the coding sequence for the viral protein which was encoded by the substituted segment.

6. The recombinant virus of claim 4, in which the substituted genomic segment contains only two units and the second unit comprises the reverse complement of an mRNA coding sequence for an heterologous protein of interest.

7. The recombinant virus according to claim 4, wherein the virus is a virus choosen among the Orthomyxoviridae, Bunyaviridae or Arenaviridae families.

8. The recombinant virus according to claim 7, wherein the virus is an influenza virus.

9. The recombinant virus of claim 8, in which the substituted genomic RNA segment of a influenza virus is the neuraminidase (NA) segment (segment 6).

10. The recombinant virus of claim 8, in which the 5'-non coding flanking sequences of the recombinant RNA segment are replaced by a longer polynucleotide RNA fragment from the 5' end of an influenza genomic RNA segment.

11. A purified polynucleotide comprising:
    a) a wild-type, truncated or mutated 3' noncoding flanking viral sequence of a genomic RNA segmented negative strand RNA virus associated upstream with the reverse complement of a viral Open Reading Frame of a segmented negative strand RNA virus,
    b) at least one sequence constituted by a wildtype, truncated or mutated 3' noncoding flanking sequence of a genomic RNA segment of a segmented negative strand RNA virus associated upstream with the reverse complement of a heterologous Open Reading Frame or a polynucleotide of interest, and
    c) a wild-type, truncated or mutated 5' non coding viral sequence.

12. A purified polynucleotide according to claim 11, comprising:
    a) a wild-type, truncated or mutated 3' noncoding flanking viral sequence of a genomic segment of a segmented negative strand RNA virus associated upstream with the reverse complement of a viral Open Reading Frame of a segmented negative strand RNA virus,
    b) at least one sequence constituted by a duplication of the same 3' noncoding flanking sequence associated upstream with a heterologous gene or a polynucleotide of interest,
    c) a wild-type, truncated or mutated 5' noncoding sequence of the same origin as the 3' noncoding sequence above.

13. A recombinant segmented negative strand RNA virus comprising a polynucleotide according to claim 11, wherein the 3' noncoding sequence, the reverse complement of a viral Open Reading Frame of a segmented negative strand RNA virus and the 5' noncoding sequence of the purified polynucleotide are chosen from the same species of segmented negative strand RNA virus.

14. A recombinant segmented negative strand RNA virus comprising a purified polynucleotide according to claim 13, which comprises a spacer located upstream the heterologous gene of interest and downstream the 5' noncoding flanking sequence, wherein said spacer corresponds to at least one or more nucleotide of the genomic RNA segment of a segmented negative strand RNA virus up to the entire sequence, said sequence has been made non coding by the disruption of its Open Reading Frame.

15. The recombinant virus according to claim 13 or 14, wherein the virus is the influenza virus.

16. A recombinant segmented negative strand virus comprising a purified polynucleotide according to claim 15, wherein viral Open Reading Frame is encoding for the neuraminidase (NA).

17. A recombinant segmented negative strand virus comprising a polynucleotide according to claim 14, wherein the spacer located upstream the heterologous gene of interest and dowstream the 5' noncoding flanking sequence corresponds to at least the reverse complement of the 39 last nucleotides plus termination codon of a coding sequence of a segmented negative strand RNA virus.

18. A recombinant influenza virus comprising a polynucleotide according to claim 15, wherein the spacer located upstream the heterologous gene of interest and downstream the 5' noncoding flanking sequence correspond at least to the reverse complement of the39 last nucleotides plus teremination codon of the neuraminidase gene of said virus.

19. A purified polypeptide encoded by a polynucleotide according to claim 1 or 11, wherein said polypeptide has the biological characteristic to induce and/or modulate and/or increase the immune response in a host against viral bacterial, fungal or tumoral diseases.

20. A viral vector, which delivers an adjuvant of immunity comprising the recombinant virus according to claim 4.

21. A viral vector, which delivers an adjuvant of immunity comprising the recombinant virus according to claim 13.

22. A viral vector, which delivers a biologically active protein according to claim 4 or 13.

23. A composition comprising a recombinant virus according to claim 4.

24. A composition comprising a recombinant virus according to claim 13.

25. A vaccine composition comprising a recombinant virus according to claim 4.

26. A vaccine composition comprising a recombinant virus according to claim 13.

27. A method for the induction in the mucosal tissues of a protective response against an infectious agent or a tumoral disease comprising the delivery of a composition according to one of claims 23 to 26.

28. A method for the induction of a protective response according to claim 27, wherein the mucosal tissue is choosen among the nasal and/or the pulmonary tissues.

29. A method for producing a recombinant virus, comprising culturing an eukaryotic cell transfected with a vector according to claims 1 or 11 said cells being infected with a parental strain of a segmented negative strand RNA virus, and recovering the recombinant virus from the resulting culture.

30. A method accoding to claim 29, wherein the recombinant virus is a recombinant influenza virus.

31. A therapeutic composition comprising a recombinant virus according to claim 4.

32. A therapeutic composition comprising a recombinant virus according to claim 13.

33. A kit comprising a composition according to claims 23 or 24.

34. A recombinant virus vNA38-CAT deposited at the C.N.C.M. on Apr. 12, 2001 under the accession number I-2657.

35. A recombinant DNA molecule corresponding to the recombinant RNA molecule according to claim 1 after reverse transcription of said RNA.

36. A recombinant DNA molecule corresponding to the recombinant viral genome of the recombinant virus according to claim 4 after reverse transcription of said RNA.

37. A process for obtaining the expression of a molecule of interest in a human or animal host or in a culture of eukaryotic cells comprising infecting said host or culture cells by a recombinant virus according to claim 4.

38. A composition comprising the recombinant RNA molecule of claim 1 and one or more pharmaceutically acceptable ingredients.

39. A composition comprising the recombinant segmented negative strand virus of claim 14 and one or more pharmaceutically acceptable ingredients.

40. A composition comprising the purified polynucleotide of claim 11 and one or more pharmaceutically acceptable ingredients.

41. A kit comprising the recombinant RNA molecule of claims 1 to 3 and one or more reagents for assaying infectivity, immune response (CTL or antibody response), gene expression, or protein levels.

42. A kit comprising recombinant segmented negative strand virus of claim 4 and one or more reagents for assaying infectivity, immune response (CTL or antibody response), gene expression, or protein levels.

43. A kit comprising the purified polynucleotide of claim 11 and one or more reagents for assaying infectivity, immune response (CTL or antibody response) gene expression, or protein levels.

44. A recombinant virus vNA38-S deposited at the CNCM on Apr. 15, 2002 under the accession number I-.

* * * * *

SEQUENCE LISTING

<160> NUMBER OF SEQ ID NOS: 18

<210> SEQ ID NO 1
<211> LENGTH: 13
<212> TYPE: DNA
<213> ORGANISM: Artificial Sequence
<220> FEATURE:
<223> OTHER INFORMATION: restriction enzyme cleavage sequence

<400> SEQUENCE: 1
ttattaggtc ttc                                                      13

<210> SEQ ID NO 2
<211> LENGTH: 13
<212> TYPE: DNA
<213> ORGANISM: Artificial Sequence
<220> FEATURE:
<223> OTHER INFORMATION: restriction enzyme cleavage sequence

<400> SEQUENCE: 2
gaagacctgg ccg                                                      13

<210> SEQ ID NO 3
<211> LENGTH: 22
<212> TYPE: DNA
<213> ORGANISM: Artificial Sequence
<220> FEATURE:
<223> OTHER INFORMATION: synthetic DNA

<400> SEQUENCE: 3
agcaaaagca ggagtttaaa tg                                            22

<210> SEQ ID NO 4
<211> LENGTH: 25
<212> TYPE: DNA
<213> ORGANISM: Artificial Sequence
<220> FEATURE:
<223> OTHER INFORMATION: synthetic DNA

<400> SEQUENCE: 4
agtagaaaca aggagttttt tgaac                                         25

```
<210> SEQ ID NO 5
<211> LENGTH: 22
<212> TYPE: DNA
<213> ORGANISM: Artificial Sequence
<220> FEATURE:
<223> OTHER INFORMATION: synthetic DNA

<400> SEQUENCE: 5
agcaaaagca ggagtttaaa tg                                              22

<210> SEQ ID NO 6
<211> LENGTH: 94
<212> TYPE: DNA
<213> ORGANISM: Artificial Sequence
<220> FEATURE:
<223> OTHER INFORMATION: synthetic DNA

<400> SEQUENCE: 6
agtagaaaca aggagttttt tgaacaaagc tagctctcga gttaaactcc tgcttttgct     60
agatctactt gtcaatggtg aacggcaact cagc                                 94

<210> SEQ ID NO 7
<211> LENGTH: 40
<212> TYPE: DNA
<213> ORGANISM: Artificial Sequence
<220> FEATURE:
<223> OTHER INFORMATION: synthetic DNA

<400> SEQUENCE: 7
gacggtctct ggccagcaaa agcaggagtt taaatgaatc                           40

<210> SEQ ID NO 8
<211> LENGTH: 40
<212> TYPE: DNA
<213> ORGANISM: Artificial Sequence
<220> FEATURE:
<223> OTHER INFORMATION: synthetic DNA

<400> SEQUENCE: 8
gacggtctca tattagtaga acaaggagt tttttgaaca                            40

<210> SEQ ID NO 9
<211> LENGTH: 36
<212> TYPE: DNA
<213> ORGANISM: Artificial Sequence
<220> FEATURE:
<223> OTHER INFORMATION: synthetic DNA

<400> SEQUENCE: 9
gacctcgagc atggagaaaa aaatcactgg gtatac                               36

<210> SEQ ID NO 10
<211> LENGTH: 30
<212> TYPE: DNA
<213> ORGANISM: Artificial Sequence
<220> FEATURE:
<223> OTHER INFORMATION: synthetic DNA

<400> SEQUENCE: 10
caggctagct acgccccgcc ctgccactca                                      30

<210> SEQ ID NO 11
<211> LENGTH: 31
<212> TYPE: DNA
<213> ORGANISM: Artificial Sequence
```

<220> FEATURE:
<223> OTHER INFORMATION: synthetic DNA

<400> SEQUENCE: 11
gacctcgagc atggtgagca agggcgagga g                          31

<210> SEQ ID NO 12
<211> LENGTH: 32
<212> TYPE: DNA
<213> ORGANISM: Artificial Sequence
<220> FEATURE:
<223> OTHER INFORMATION: synthetic DNA

<400> SEQUENCE: 12
caggctagct acttgtacag ctcgtccatg cc                         32

<210> SEQ ID NO 13
<211> LENGTH: 61
<212> TYPE: DNA
<213> ORGANISM: Artificial Sequence
<220> FEATURE:
<223> OTHER INFORMATION: synthetic DNA

<400> SEQUENCE: 13
gacctcgagc atgggacatc atcatcatca tcatgttcta tcaggtgagg atggtggtgt   60
c                                                           61

<210> SEQ ID NO 14
<211> LENGTH: 36
<212> TYPE: DNA
<213> ORGANISM: Artificial Sequence
<220> FEATURE:
<223> OTHER INFORMATION: synthetic DNA

<400> SEQUENCE: 14
caggctagct acggatagag agtccattgc caaaaa                     36

<210> SEQ ID NO 15
<211> LENGTH: 36
<212> TYPE: DNA
<213> ORGANISM: Artificial Sequence
<220> FEATURE:
<223> OTHER INFORMATION: synthetic DNA

<400> SEQUENCE: 15
gacgctagct ggccagacgg tgctgagttg ccgttc                     36

<210> SEQ ID NO 16
<211> LENGTH: 23
<212> TYPE: DNA
<213> ORGANISM: Artificial Sequence
<220> FEATURE:
<223> OTHER INFORMATION: synthetic DNA

<400> SEQUENCE: 16
gtgagcggat aacaatttca cac                                   23

<210> SEQ ID NO 17
<211> LENGTH: 32
<212> TYPE: DNA
<213> ORGANISM: Artificial Sequence
<220> FEATURE:
<223> OTHER INFORMATION: synthetic DNA -continued

```
<400> SEQUENCE: 17
gacctcgaga acatggagaa catcacatca gg                              32

<210> SEQ ID NO 18
<211> LENGTH: 35
<212> TYPE: DNA
<213> ORGANISM: Artificial Sequence
<220> FEATURE:
<223> OTHER INFORMATION: synthetic DNA

<400> SEQUENCE: 18
caggctagct aaatgtatac ccaaagacaa aagaa                           35
```